US009283542B2

(12) United States Patent
Yamamoto et al.

(10) Patent No.: US 9,283,542 B2
(45) Date of Patent: Mar. 15, 2016

(54) CHROMATOGRAPHY MEDIUM, PREPARATION METHOD OF THE SAME, AND METHOD FOR PRODUCING VIRUS VACCINE USING THE CHROMATOGRAPHY MEDIUM

(75) Inventors: Yuka Yamamoto, Kumamoto (JP);
Yuichi Yamamoto, Kumamoto (JP);
Yasuto Umeda, Kumamoto (JP);
Shigeyuki Aoyama, Kumamoto (JP);
Yoshihiro Matsumoto, Kumamoto (JP)

(73) Assignee: JNC CORPORATION, Tokyo (JP)

( * ) Notice: Subject to any disclaimer, the term of this patent is extended or adjusted under 35 U.S.C. 154(b) by 983 days.

(21) Appl. No.: 12/822,401

(22) Filed: Jun. 24, 2010

(65) Prior Publication Data

US 2010/0330119 A1 Dec. 30, 2010

(30) Foreign Application Priority Data

Jun. 25, 2009 (JP) ................................ 2009-151290
Mar. 26, 2010 (JP) ................................ 2010-071319

(51) Int. Cl.
| | |
|---|---|
| C12N 7/00 | (2006.01) |
| B01J 20/286 | (2006.01) |
| B01J 20/285 | (2006.01) |
| B01D 15/26 | (2006.01) |
| B01J 20/26 | (2006.01) |
| B01J 20/28 | (2006.01) |
| B01J 20/32 | (2006.01) |

(52) U.S. Cl.
CPC ............. *B01J 20/286* (2013.01); *B01D 15/265* (2013.01); *B01J 20/267* (2013.01); *B01J 20/285* (2013.01); *B01J 20/28016* (2013.01); *B01J 20/328* (2013.01); *B01J 20/3212* (2013.01); *B01J 20/3272* (2013.01); *C12N 7/00* (2013.01); *B01J 2220/44* (2013.01); *C12N 2760/16151* (2013.01)

(58) Field of Classification Search
CPC .................... A61K 2300/00; A61K 2039/505; C07K 2317/92; C07K 1/22; B01L 3/5027
See application file for complete search history.

(56) References Cited

U.S. PATENT DOCUMENTS

| | | | |
|---|---|---|---|
| 4,178,439 A | 12/1979 | Ayers et al. | |
| 4,480,091 A | 10/1984 | Brewer | |
| 4,576,928 A * | 3/1986 | Tani et al. ...................... 502/404 |
| 4,724,210 A | 2/1988 | Oka et al. | |
| 4,725,546 A | 2/1988 | Sakamoto et al. | |
| 5,447,859 A | 9/1995 | Prussak | |
| 5,667,684 A | 9/1997 | Motomura et al. | |
| 6,149,917 A | 11/2000 | Fanget et al. | |
| 6,537,793 B2 | 3/2003 | Blanche et al. | |
| 2007/0213258 A1* | 9/2007 | Nakayama et al. ................ 514/8 |
| 2009/0062118 A1* | 3/2009 | Umeda et al. .................. 502/404 |

FOREIGN PATENT DOCUMENTS

| | | | |
|---|---|---|---|
| EP | 0171086 | | 2/1986 |
| EP | 1808697 | | 7/2007 |
| GB | 2429708 | | 3/2007 |
| JP | 61-047185 | | 3/1986 |
| JP | 61-47186 | | 3/1986 |
| JP | 07-289891 | | 11/1995 |
| JP | 09-503123 | | 3/1997 |
| JP | 11-510151 | | 9/1999 |
| JP | 2001-190273 | | 7/2001 |
| JP | 2006-274245 | | 10/2006 |
| WO | 0121151 | | 3/2001 |
| WO | WO 2005/074729 | * | 8/2005 |
| WO | 2008-039136 | | 4/2008 |
| WO | 2008/125361 | | 10/2008 |
| WO | WO2008/125360 | | 10/2008 |

OTHER PUBLICATIONS

Authored by Kalbfuss, et al., article titled "Purification of Cell Culture-Derived Human Influenza A Virus by size-exclusion and anion-exchange chromatography, " adopted from Biotechnology and Bioengineering, 96 No. 5, Apr. 1, 2007, pp. 932-944.
Authored by Opitz, et al., article titled "Impact of adsorbents selection on capture efficiency of cell culture derived human influenza viruses, " adopted from Journal of Biotechnology 131 (2007), pp. 309-317.
Authored by O'Neil, et al., article titled "Virus Harvesting and affinity-based liquid chromatography, " adopted from Nature Bio/technology vol. 11 Feb. 1993, pp. 173-178.
Authored by Hermanson, et al., article titled "Immobilized Affinity Ligand Techniques, " Academic Press Inc. 1992.
"Office Action of European Counterpart Application", issued on Sep. 9, 2014, p. 1-8.
"Search Report of European Counterpart Application", issued on Aug. 30, 2011, p. 1-10, in which the listed references were cited.
Miletich et al, "The Synthesis of Sulfated Dextran Beads for Isolation of Human Plasma Coagulation Factors II, IX, and X", Analytical Biochemistry, Jun. 1, 1980, p. 304-310, vol. 105, No. 1.
Anonymous, "Sepharose and Sepharose CL Gel Filtration Media—Product Information", Mar. 1, 2003, p. 1-3, Retrieved from: http://www.sigmaaldrich.com/etc/medialib/docs/Sigma/Product_Information_Sheet/cl6b200pis.Par.0001.File.tmp/c16b200pis.pdf, retrieved on Aug. 16, 2011.
Anonymous, "Sephadex LH-20", Mar. 1, 2006, p. 1-2, Retrieved from: http://www.gelifesciences.com/aptrix/upp00919.nsf/Content/E1EAFB82CA45CBF2C1257628001DOC85/$file/56119097AD.pdf, retrieved on Aug. 16, 2011.
Neil et al., "Virus Harvesting and Affinity-Based Liquid Chromatography", Bio/Technology, Feb. 1, 1993, p. 173-178, vol. 11.

* cited by examiner

Primary Examiner — Benjamin P Blumel
(74) Attorney, Agent, or Firm — J.C. Patents

(57) ABSTRACT

A Chromatography medium having the properties of high virus adsorption and high fluidity, and a method for producing a virus vaccine using these are provided. The Chromatography medium is formed by binding a sulfated polysaccharide to porous particles having an exclusion limit molecular weight of 6000 Da or less when pure water is used as mobile phase and standard polyethylene glycol is used and an average particle size in the range of 30-200 μm.

5 Claims, 2 Drawing Sheets

CHROMATOGRAPHY MEDIUM, PREPARATION METHOD OF THE SAME, AND METHOD FOR PRODUCING VIRUS VACCINE USING THE CHROMATOGRAPHY MEDIUM

CROSS-REFERENCE TO RELATED APPLICATION

This application claims the priority benefits of Japan patent application serial no. 2009-151290, filed on Jun. 25, 2009, and application serial no. 2010-071319, filed on Mar. 26, 2010. The entirety of each of the above-mentioned patent applications is hereby incorporated by reference herein and made a part of specification.

BACKGROUND OF THE INVENTION

1. Field of the Invention

The present invention generally relates to a liquid chromatography medium, a preparation method of the same, and a method for producing virus vaccine using the chromatography medium.

2. Description of Related Art

In recent years, development of biological preparation with various animals, insect cells, or microorganisms as hosts is significant. The productivity of biological preparation has been improved by high-volume fermentation and high-efficiency fermentation, thus the efficiency of the corresponding purification step is also required to be improved. Especially, as a purification process of cell-culture production, the production of biological preparation using a chromatography method has aroused great interest, and the chromatography medium for purification is expected to achieve high fluidity and high adsorption at a lowered cost.

In the field of production of vaccines against viral diseases, new manufacturing processes or production methods are also studied to replace previous methods. For example, in the field of manufacturer of influenza vaccines, efforts are focused on cell culture methods having the advantage of providing the product in a shorter period of time than the previous egg culture method. With such a change in the virus culture process, new purification processes are also studied. Particularly, chromatography methods have aroused great interest, which is capable of conveniently producing a preparation of high purity.

For example, in Non-patent Reference 1 (Biotechnology and Bioengineering 96 (2006), 932-944), purification of influenza virus cultured with Madin-Darby canine kidney (MDCK) cells by using anion exchange chromatography is reported. In Non-patent Reference 2 (J. Biotechnology 13 (2007), 309-317), adsorption of influenza virus from MDCK cells by chromatography utilizing the affinity property of lectin is proposed. Moreover, in Patent Reference 1 (Japanese Patent Publication No. 1999-51051), an example of industrial production method of Japanese Encephalitis virus from Vero cells by chromatography is disclosed.

In the field of virus adsorption and purification, efforts are made to attempts of using sulfated polysaccharides. For example, in the purification of influenza virus in Patent Reference 2 (Japanese Patent Publication No. 1986-47186), and the purification of Japanese Encephalitis virus in Patent Reference 3 (Japanese Patent Publication No. 1986-47185), cellulose particles sulfated with chlorosulfonic acid are used as gel for chromatography.

Such cellulose sulfate is also used as a ligand of chromatography medium in Patent Reference 4 (European Patent Application Publication No. 1808697), to concentrate influenza virus particles obtained from cell culture. In this reference, Cellufine Sulfate with sulfated ester as active group (manufactured by Chisso Corp.) is used as microporous cellulose particles having an exclusion limit molecular weight of 2000-4000 Da.

Furthermore, in Patent Reference 5 (International Publication No. 2008-125361), an example in which influenza virus particles from cell culture is purified by using a membrane formed by partially sulfating a cellulose membrane with chlorosulfonic acid is disclosed. Moreover, in Patent Reference 6 (Japanese Patent Publication No. 1997-503123), a method for preparing a gel suitable for adsorbing enveloped virus by controlling the introduced amount of sulfate group into the sulfated polysaccharide to be about 6 µmol/g is disclosed.

Furthermore, efforts are also made to develop a material suitable for adsorbing virus by supporting polysaccharide on the surface of particles. For example, in Patent Reference 7 (Japanese Patent Publication No. 1995-289891), an example in which a material suitable for adsorbing human immunodeficiency virus (HIV) is prepared by binding dextran sulfate onto porous polypropylene membrane is disclosed.

Moreover, in Patent Reference 8 (U.S. Pat. No. 6,537,793), an example of separating adenovirus by using chromatography medium is disclosed, in which the chromatography medium imparts flexible dextran arms to agarose particles for introducing ion exchange groups.

Furthermore, in Patent Reference 9 (International Publication No. 2008-039136), chromatography medium for purification of influenza virus developed by imparting sulfated dextran fibre to agarose particles is disclosed. When the medium is used, the troublesome separation of nucleic acid derived from the host cell with the influenza virus in preparation of vaccine can be improved.

Moreover, in Patent Reference 10 (Japanese Patent Publication No. 2001-190273), particles for concentrating virus prepared by binding sulfated polysaccharides insoluble in water to polystyrene particles is disclosed.

As shown in the above references, sulfated polysaccharides, especially cellulose sulfate, has high use value in the field of purification and concentration of enveloped virus such as HIV or influenza virus. For example, sulfated cellulose particles produced by introducing sulfate groups into cellulose particles by using suitable sulfating agents such as chlorosulfonic acid are sold under trade name Cellufine Sulfate by Chisso Corp. Cellufine Sulfate is useful as a chromatography medium, and in Reference 3, the adsorption of cellufine sulfate for various viruses is evaluated, and the application of cellufine sulfate in the field of purification of influenza virus are under development.

However, when direct introducing sulfate group into cellulose particles, the cellulose particles are simultaneously softened due to the hydrophilicity of the sulfate group, thus leading to the decrease of the fluidity, which is one of the important properties in chromatography. Therefore, the introduction of sulfate group has an upper limit.

Furthermore, as indicated in a comparative example in Patent Reference 5, the potential of insufficient adsorption capability exists for different strains of influenza viruses. The influenza virus has variety species based on the difference of H type, N type, and combinations thereof. Therefore, it can be expected that in production of influenza vaccine, the culture conditions of the varies is required to be different for each strain, and the purification process and conditions of vaccine are required to be individually studied for each strain. If chromatography medium with improved virus adsorption capability is used, constant level of adsorption can be ensured, thus it can be expected that the complexity of research of individual process will be correspondingly decreased.

As a result, in recent years, a new vaccine derived from cell culture is used to replace the previous egg culture. However, the vaccine manufacturers want to obtain a target of high purity with proteins and nucleic acids derived from the host cell removed. Therefore, as described above, high selectivity is required for the chromatography medium used in vaccine production.

REFERENCES IN PRIOR ART

Patent References

[Patent Reference 1] Japanese Patent Publication No. 1999-51051
[Patent Reference 2] Japanese Patent Publication No. 1986-47186
[Patent Reference 3] Japanese Patent Publication No. 1986-47185
[Patent Reference 4] European Patent Application Publication No. 1808697
[Patent Reference 5] International Publication No. 2008-125361
[Patent Reference 6] Japanese Patent Publication No. 1997-503123
[Patent Reference 7] Japanese Patent Publication No. 1995-289891
[Patent Reference 8] U.S. Pat. No. 6,537,793
[Patent Reference 9] International Publication No. 2008-039136
[Patent Reference 10] Japanese Patent Publication No. 2001-190273

Non-Patent References

[Non-patent Reference 1] Biotechnology and Bioengineering 96 (2006), 932-944
[Non-patent Reference 2] J. Biotechnology 13 (2007), 309-317
[Non-patent Reference 3] Nature Bio/technology 11 (1993), 173-178

SUMMARY OF THE INVENTION

Accordingly, the present invention is directed to chromatography medium for adsorbing virus with improved adsorption and fluidity performances and having sulfate group as ligand. The present invention is further directed to a method for producing a virus vaccine, and especially a method for producing an influenza virus vaccine using the chromatography medium of the present invention.

The inventors endeavored to the study of the technical problems in the prior art. It was found that a chromatography medium with improved adsorption and fluidity could be obtained by binding sulfated polysaccharides to a porous particles having an exclusion limit molecular weight of 6000 Da or less when pure water is used as mobile phase and standard polyethylene glycol is used and an average particle size in the range of 30-200 μm. Furthermore, it was understood that if the virus vaccine production method includes a step of purifying virus particles with the chromatography medium, then the adsorption of impurities such as deoxyribonucleic acid (DNA) from the host cell on the chromatography medium could be reduced, thus the influenza virus vaccine could be obtained with a very high efficiency. The inventors accomplished the present invention based on the knowledge above.

The present invention provides chromatography medium, a preparation method of the same, and a method for producing a virus vaccine using the chromatography medium, which are as described below.

The present invention can be implemented by the following technical solutions.

[1] A chromatography medium, formed by binding a sulfated polysaccharide to porous particles having an exclusion limit molecular weight of 6000 Da or less when pure water is used as mobile phase and standard polyethylene glycol is used and an average particle size in the range of 30-200 μm.

[2] The chromatography medium according to Item [1], where the porous particles are cross-linked with the sulfated polysaccharide by using a cross-linking agent having two or more functional groups.

[3] The chromatography medium according to Item [1] or [2], where the porous particles have an average particle size in the range of 40-120 μm.

[4] The chromatography medium according to any one of Items [1] to [3], where the porous particles are cellulose particles.

[5] The chromatography medium according to any one of Items [1] to [4], where a limiting viscosity of the sulfated polysaccharide is in the range of 0.21-0.90 dL/g.

[6] The chromatography medium according to any one of Items [1] to [5], where the sulfated polysaccharide is one or more selected from cellulose sulfate, dextran sulfate, and pullulan sulfate.

[7] The chromatography medium according to Item [2], where the cross-linking agent having two or more functional groups is a bivalent or multivalent cross-linking agent having at least one or more glycidyl groups.

[8] The chromatography medium according to Item [7], where the bivalent or multivalent cross-linking agent having at least one or more glycidyl groups is epichlorohydrin.

[9] The chromatography medium according to any one of Items [1] to [8], where a content of sulfur is in the range of 0.2-6% by weight percent (wt %).

[10] A method for preparing the chromatography medium according to Item [2], including:
step 1: cross-linking porous particles with a polysaccharide by using a cross-linking agent having two or more functional groups, to obtain polysaccharide-binding porous particles; and
step 2: sulfating the polysaccharide-binding porous particles obtained in step 1 with a sulfating agent.

[11] The method for preparing the chromatography medium according to Item [10], where the porous particles have an average particle size in the range of 40-120 μm.

[12] The method for preparing the chromatography medium according to Item [10] or [11], where the porous particles are cellulose particles.

[13] The method for preparing the chromatography medium according to any one of Items [10] to [12], where the polysaccharide is water-soluble, and has a limiting viscosity in the range of 0.21-0.90 dL/g.

[14] The method for preparing the chromatography medium according to any one of Items [10] to [13], where the polysaccharide is one or more selected from dextran and pullulan.

[15] The chromatography medium according to Item [1], represented by General Formula (1) below:

$$X\text{—}O\text{—}CH_2\text{—}C(OH)H\text{—}CH_2\text{—}NH\text{—}CH_2\text{—}Z \quad \text{Formula (1)}$$

(in Formula (1), X is a cellulose particle having an average particle size in the range of 40-120 μm, O bonded to X is an oxygen originating from hydroxyl of cellulose, Z is cellulose sulfate, and C bonded to Z is a carbon originating from the reductive end aldehyde of cellulose sulfate).

[16] The chromatography medium according to Item [15], where the sulfur content in cellulose sulfate is 15 wt % or more, and the viscosity of an aqueous solution of 1 wt % at 20° C. is in the range of 15-300 MPa/sec.

[17] A method for producing a virus vaccine, where the virus particles are separated and purified by using the chromatography medium according to any one of Items [1] to [9], [15] and [16].

[18] The method for producing a virus vaccine according to Item [17], capable of inhibiting adsorption of DNA to the chromatography medium.

[19] The method for producing a virus vaccine according to Item [17] or [18], where the virus particles are influenza virus.

Effects of the Invention

According to the present invention, chromatography medium having high virus adsorption and high fluidity can be obtained. Therefore, if the virus vaccine production method includes a step of separating and purifying virus particles with the chromatography medium of the present invention, the virus vaccine can be obtained with a very high efficiency, and high separation and purification efficiency can be expected, especially for influenza virus vaccine.

In order to make the features and advantages of the present invention more clearly and comprehensible, the present invention is described below in detail through the following embodiments with reference to the accompanying drawings.

BRIEF DESCRIPTION OF THE DRAWINGS

The accompanying drawings are included to provide a further understanding of the invention, and are incorporated in and constitute a part of this specification. The drawings illustrate embodiments of the invention and, together with the description, serve to explain the principles of the invention.

DESCRIPTION OF THE EMBODIMENTS

Figure 1:
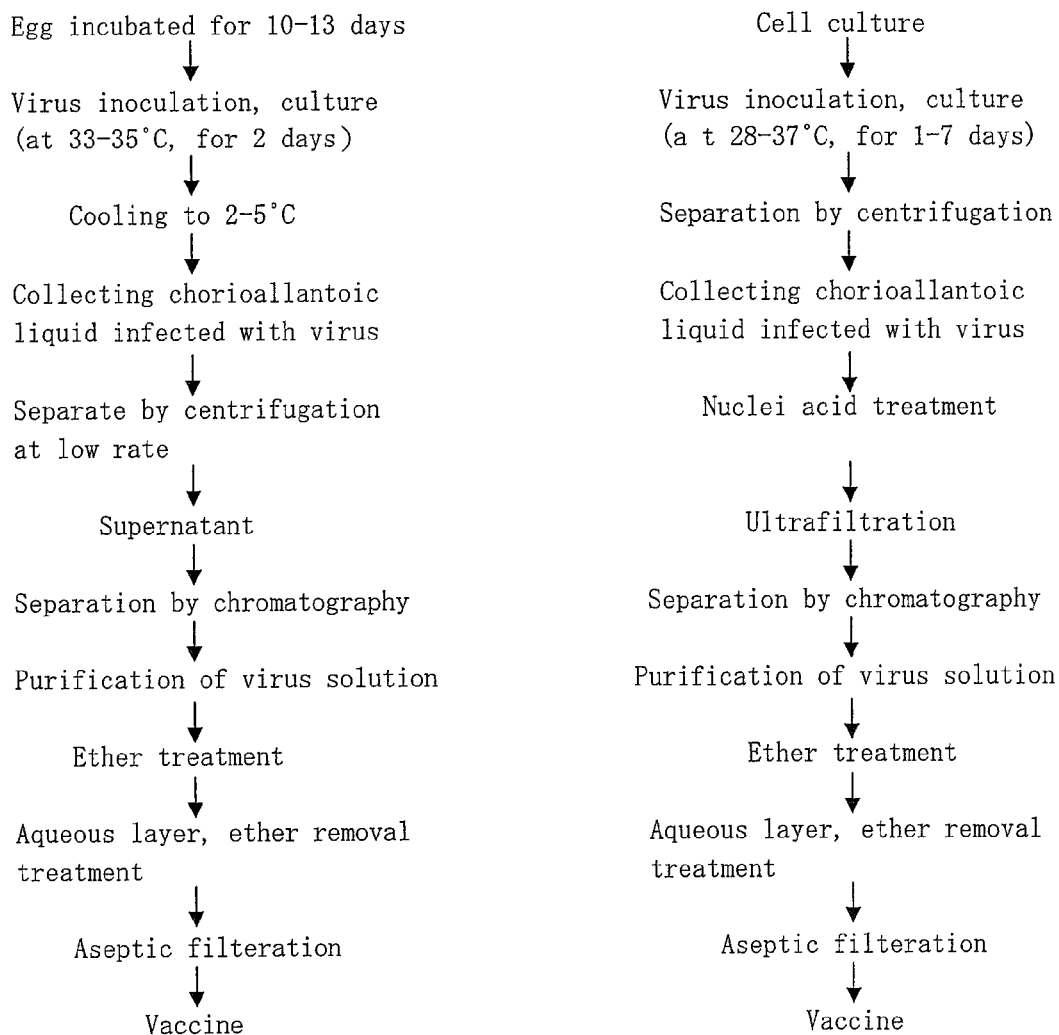
FIG. 1 is a manufacturing process flow of influenza vaccine.

Reference will now be made in detail to the present embodiments of the invention, examples of which are illustrated in the accompanying drawings. Wherever possible, the same reference numbers are used in the drawings and the description to refer to the same or like parts.

Hereinafter, the present invention will be described in detail.

The chromatography medium of the present invention is a complex formed by binding sulfated polysaccharides to porous particles having specified particle size and pore size.

The sulfated polysaccharides can be bound to the porous particles at any site, and preferably on the surface rather than in the micropore of the porous particles, where higher separation and purification capability of virus is desired.

By selecting the pore size of the porous particles, the molecular weight and the limiting viscosity of the sulfated polysaccharide, the sulfated polysaccharide can be arranged on the surface of the porous particles with a high efficiency. Accordingly, the sulfate group required in binding the virus particles is introduced to the surface of the particles with a high efficiency. The inventors considered that viruses represented by influenza viruses could be preferably adsorbed as a result of the increased density of sulfate group as ligand by the means above.

That is, in the present invention, the porous particles are preferably combined with sulfated polysaccharides having molecular weight or limiting viscosity higher than the exclusion limit of the porous particles, and more preferably, microporous particles are combined with sulfated polysaccharide having high molecular weight or high limiting viscosity. Moreover, the adsorption performance of the virus, and especially the influenza virus, can be improved by controlling the introduced amount of sulfate group. Furthermore, in order to effectively eliminate the influence of impurities from the host such as nucleic acid or protein, the density of the sulfate group as ligand can be increased.

In the present invention, the binding of the porous particles with the sulfated polysaccharides have no particular limit. Hereinafter, an example is first described in detail, in which cellulose sulfate (sulfated polysaccharide) is bound to cellulose particles (porous particles) with the reductive end (sometimes referred to as "Binding Reaction 1", hereinafter).

Addition reaction of cellulose sulfate to cellulose particles is preferably achieved by introducing amino group into the cellulose particles, mixing the cellulose particles with cellulose sulfate in neutral or weak basic aqueous solution, to form Schiff base, and then reducing the Schiff base with a reductive agent such as dimethyl aminoborane.

Introduction of amino group to a cellulose particles can be achieved by, for example, reacting the cellulose particles with epichlorohydrin under basic condition, followed by reacting with aqueous ammonia, in which are described in Immobilized Affinity Ligand Techniques written by Hermason et al. (Academic Press Inc. 1992).

A particularly preferred aspect of the chromatography medium thus prepared in the present invention is represented by General Formula (1) below:

$$X-O-CH_2-C(OH)H-CH_2-NH-CH_2-Z \qquad \text{Formula (1).}$$

In Formula (1), X is a cellulose particle having an average particle size in the range of 40-120 μm, O bonded to X is a oxygen originating from hydroxyl of cellulose, Z is cellulose sulfate, and C bonded to Z is a carbon originating from the reductive end aldehyde of cellulose sulfate.

As shown in Reaction Formula (1) below, O (oxygen) bonded to X is aminated by aqueous ammonia after the addition reaction of epichlorohydrin. Next, the amino group is reacted with the reductive end X of cellulose sulfate, to form a Schiff base, which can be stabilized by, for example, a reductive agent such as dimethyl aminoborane.

Reaction Formula (1)

$$\text{celluose (X)-OH} + \underset{}{\overset{O}{\triangle}}\diagdown Cl \longrightarrow$$

$$\text{cellulose (X)-O}\diagdown\underset{}{\overset{O}{\triangle}} \xrightarrow{\text{aqueous ammonia}}$$

$$\text{cellulose (X)-O}\diagdown\underset{OH}{}\diagup NH_2 \xrightarrow{Z-CHO} \xrightarrow{(CH_3)_2NHBH_3}$$

-continued

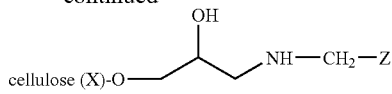

It can be concluded that the chromatography medium represented by General Formula (1) has cellulose sulfate capable of binding virus particles and bound to the surface of cellulose particles with the reductive end as a starting point in the form of a brush. Cellulose sulfate bound in such a manner is bound at its end, thus having high degree-of-freedom, such that an excellent binding with (identification of) virus particles and especially influenza virus particles can be expected.

Next, another preferred binding reaction in the present invention is described. The binding reaction is to bind sulfated polysaccharides to porous particles by using cross-linking agents having two or more functional groups (sometimes referred to as "Binding Reaction 2" hereinafter). Such binding can be achieved by binding polysaccharides to porous particles to form complex, and then sulfating the complex with a sulfating agent (sometimes referred to as "Binding Reaction 2A" hereinafter), or by binding sulfated polysaccharides to porous particles (sometimes referred to as "Binding Reaction 2B" hereinafter). In the present invention, in view of low production cost, the Binding Reaction 2A is preferred due to the high price of the sulfated polysaccharides. Thus, in Binding Reaction 2A, when the porous particles used as supporter is sulfated particles, sulfate group also can be introduced to the porous particles. In the present invention, in view of easy control of the induction of sulfate group, Binding Reaction 2A is preferred, compared with Binding Reaction 2B.

Furthermore, the binding of the porous particles with polysaccharides or sulfated polysaccharides are preferably carried out in solvent in the presence of alkali to utilize the reactivity of the glycidyl group. Especially, when the polysaccharide is water-soluble, it is preferably carried out in the presence of alkali.

Hereinafter, an example of the Binding Reaction 2A is described in detail in which the polysaccharide is water-soluble and the porous particles are cellulose. Any cross-linking agents can be used provided that the cross-linking agents have two or more functional groups. An active group is introduced into the cellulose particles in alkaline aqueous solution, and then the introduced active group is reacted with the water-soluble polysaccharides, to obtain water-soluble polysaccharides-binding cellulose particles (complex). In view of low cost, convenience in use, and low residue, the suitable alkali is, for example, sodium hydroxide or potassium hydroxide, with sodium hydroxide being particularly suitable. In this case, the solvent is preferably water.

In the present invention, any cross-linking agents can be used provided that the cross-linking agents have multiple functional groups. However, in view of the chemical stability in binding with cellulose, or in view of preventing non-specific adsorption, cross-linking agents having no heteroatoms such as nitrogen or sulfur or having no double bonds of hydrophobicity or no medium to long chain alkyl are preferred. Examples for such cross-linking agents include multifunctional cross-linking agents having halogen atom and glycidyl group, such as epichlorohydrin and epibromohydrin; or glycidyl ether cross-linking agents, such as allyl glycidyl ether, glycerol triglycidyl ether, and glycerol diglycidyl ether. Particularly, epichlorohydrin is preferably used, due to small molecular weight, low cost, and high reactivity. Furthermore, an inorganic salt such as sodium sulfate can also coexist in the reaction solution, in order to improve the reaction efficiency.

Moreover, in Japanese Patent Publication No. 1985-77769, a method for binding water-soluble polysaccharide to porous cellulose particles is disclosed, in which the cross-linked cellulose particles are reacted with epichlorohydrin to introduce an epoxide group, and then the particles are reacted with polysaccharide such as dextran or pullulan, to bind the polysaccharide to the cellulose particles. The method can be used in the present invention.

For the water-soluble polysaccharide-binding cellulose particles thus prepared, the introduction of sulfate group in the polysaccharides is achieved by reacting a sulfating agent such as chlorosulfonic acid-pyridine complex and anhydrous sulfuric acid-dimethyl formamide complex with the water-soluble polysaccharide-binding cellulose particles. Specifically, a generally known method can be used, such as those disclosed in U.S. Pat. No. 4,480,091 or Japanese Patent Publication No. 2006-274245, that is, sulfating water-soluble polysaccharide-binding cellulose particles by reacting with anhydrous sulfuric acid or chlorosulfonic acid in a solvent such as dimethyl formamide or pyridine to form a complex.

The amount of the sulfating agent used varies with the sulfur content in the target particles and the reaction conditions, and the content of the sulfating agent is preferably in the range of 10-100 weight parts, and more preferably 10-50 weight parts, based on 100 weight parts of cellulose particles. The reaction time also varies with the species of the solvent and the sulfating agent, and is preferably 0.5-24 hr under an inert atmosphere at 0-100° C., and preferably 20-85° C. When the chlorosulfonic acid-pyridine complex used in the embodiments is used as sulfating agent, the reaction time is preferably in the range of 0.5-10 hr due to the high reactivity.

After the reaction, the water-soluble polysaccharide-binding cellulose particles having sulfate group introduced are separated from the reaction solution by, for example, filtration, neutralized with, for example, NaOH, and then washed with pure water several times, so as to obtain chromatography medium used in the present invention.

Figure 3:
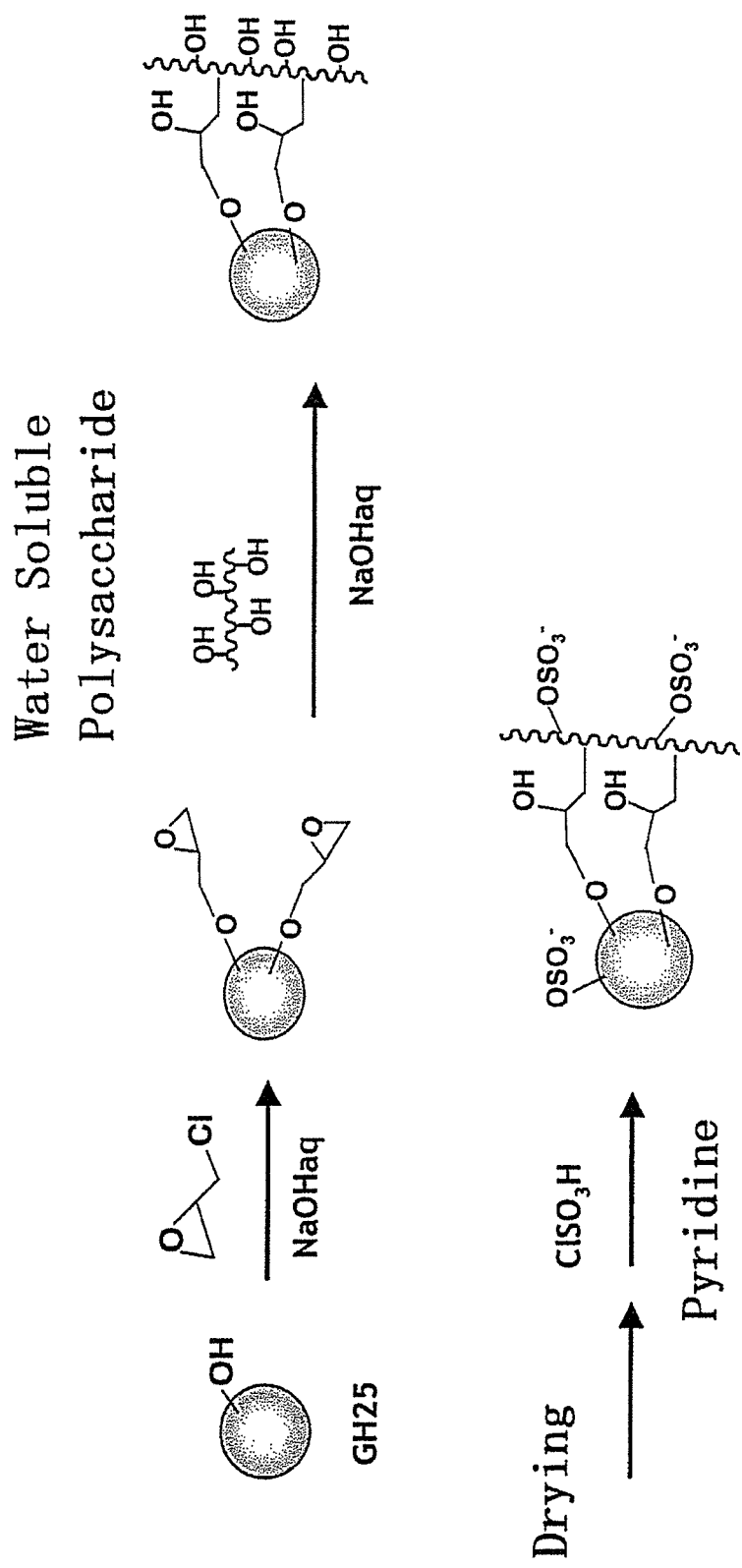
FIG. 3 is a schematic view of Binding Reaction 2A.

Binding Reaction 2A is described in more detail with an example in which GH25 (trade name) manufactured by Chisso Corp. is used as the cellulose particles (FIG. 3).

A method for conveniently and preferably binding the water-soluble polysaccharides to GH25 includes: introducing epoxide group into GH25, washing and recovering, and then mixing with a water-soluble polysaccharide in an alkaline aqueous solution. In this case, the water-soluble polysaccharide is preferably dissolved into water in advance, in view of the operation and uniformity of the reaction.

When introducing an epoxide group into GH25, GH25 is reacted with epichlorohydrin under alkaline condition, as described in Immobilized Affinity Ligand Techniques (p 181-183) written by Hermason et al. (Academic Press Inc. 1992).

The binding amount of the water-soluble polysaccharides to GH25 can be controlled by individually or simultaneously adjusting the concentration of the added water-soluble polysaccharides and the introduced amount of the epoxide group. GH25 is preferably dissolved to a content of 15-20 wt %, and the introduced amount of the epoxide group is preferably in the range of 100-300 mmol per gram of dry GH25. The introduced amount of the epoxide group can be controlled by the amount of epichlorohydrin added in the reaction system. The introduced amount can be achieved by, for example, setting the added ratio of GH25 to epichlorohydrin in the range of 3-10 mol/mol in the presence of alkali of 3 wt % at reaction temperature of 30° C.

The introduction of the sulfate group into thus prepared GH25 having water-soluble polysaccharide bound on the surface can be achieved by, for example, the method as described in Japanese Patent Publication No. 1986-47185 or Japanese Patent Publication No. 1995-196702. The introduced amount of sulfate group can be easily changed by adjusting the added ratio of chlorosulfonic acid, especially in the reaction in which chlorosulfonic acid is used as sulfating agent in pyridine, thus being preferred.

The introduced amount of the sulfate group in the porous cellulose particles can be suitably selected according to the culturing conditions, the affinity for the purified target, and the amount of charge. In case when the influenza virus is adsorbed and purified, for example, the sulfur content is preferably 0.2-6 wt %, based on the obtained chromatography medium.

The preparation method of the chromatography medium of the present invention is not limited to Binding Reaction 1 and Binding Reaction 2, and is generally classified into two types according to the polysaccharide bound to the porous particles: 1) the polysaccharide is sulfated polysaccharide (Binding Reaction 1 and Binding Reaction 2B, sometimes collectively called as "Preparation Method I" hereinafter), and 2) the polysaccharide is bound and then sulfated (Binding Reaction 2A, sometimes called as "Preparation Method II" hereinafter).

Any porous particles can be used provided that the porous particles used in the present invention are practically effective as chromatography medium. The example of the porous particles includes, for example, silica gel, methacrylic acid gel, agarose gel, and cellulose gel. Particularly, in view of the applicability in practice and tolerance to alkali, as chromatography medium for purification of virus, the cellulose particles obtained by granulating cellulose having high chemical stability are suitable to serve as the porous particles of the present invention.

The porous particles used in the present invention have an average particle size in the range of 30-200 μm, preferably 40-120 μm, and more preferably 50-100 μm.

The particle size can be adjusted to the range desired by, for example, grading with a sieve of Japanese Industrial Standard (JIS), and particularly preferably grading by using sieves with mesh sizes of 45 μm (wire diameter 0.03 mm) and 106 μm (wire diameter 0.075 mm).

The average particle size of the porous particles is a mean value of a long diameter of any 200 particles taken by a scanning electron microscope (SEM) or an optical microscope.

Furthermore, the sphericity (short diameter/long diameter) of the porous particles used in the present invention has no particular limit, and is preferably 0.8-1.0.

The preparation method of the porous cellulose particles suitable in the present invention has no particular limit, and includes, for example, a method for preparing a cellulose particles with cellulose acetate disclosed in Japanese Patent Publication No. 1980-39565 or Japanese Patent Publication No. 1980-40618; or a method for granulating cellulose in a solution of calcium thiocyanate disclosed in Japanese Patent Publication No. 1988-62252.

Furthermore, in order to improve the physical stability of the cellulose particles, the cellulose for forming particles is preferably cross-linked by using a cross-linking agent. The cross-linking method has no particular limit as long as it is useful in cross-linking the cellulose. The example of the cross-linking agent includes multiple functional compounds such as epichlorohydrin.

The exclusion limit molecular weight of the porous particles used in the present invention is measured to be 6000 Da or less when pure water is used as mobile phase and standard polyethylene glycol is used. The exclusion limit molecular weight is an index indicating the size of the pore (sometimes referred to as "micropore" hereinafter) opened on the porous particles. Though the reason cannot be expounded clearly, it is generally accepted that when the exclusion limit molecular weight above is 6000 Da or less, as a ligand, the bound sulfated polysaccharides is difficult to enter inside of the porous particles, and is actually remained on the surface of the porous particles.

More particularly, the exclusion limit molecular weight is the lowest molecular weight of a molecule that cannot enter the micropore in a gel permeation chromatograph, and can be determined by studying the relationship between the molecular weight with the eluting volume by using compounds of various molecular weights. Example of the determination method of the exclusion limit molecular weight includes those described in, for example, Biochemical Experiment Method 2: Gel Chromatography ($1^{st}$ Edition, p 7-17) written by L. Fischer (Tokyo Kagaku Dojin). The specific determination method in the present invention is as shown in the embodiments.

Furthermore, in the present invention, polyethylene glycol used to determine the exclusion limit molecular weight is preferably, for example, standard polyethylene glycol PEG-19000, PEG-8650, PEG-4120, PEG-590, and PEG-220 (all are trade names) manufactured by POLYMER LABORATORIES Ltd.

In the present invention, commercially available cellulose particles are preferably used as porous particles. For example, the non-cross-linked spherical Cellufine GH-25 (trade name) manufactured by Chisso Corp. is particularly preferably used in the present invention, as it meets the required conditions correlated with the exclusion limit molecular weight, thus meeting the required conditions correlated with the average particle size. Moreover, GH-25 also can be cured through a cross-linking reaction, so as to meet the required conditions above.

In the present invention, the exclusion limit molecular weight may not be the initial exclusion limit molecular weight of the porous particles. For example, the cellulose particles having a high exclusion limit molecular weight obtained by the method described in Japanese Patent Publication No. 63-62252 is added with a water-soluble polymer such as dextran or pullulan by multivalent cross-linking agents such as epichlorohydrin, and gelled in the micropore, thereby exhibiting an exclusion limit molecular weight value specified in the present invention, and thus being applicable in the present invention.

Moreover, in the Preparation Method II, when the porous particles are reacted with the sulfating agent, the sulfation of the porous particles and polysaccharides can be carried out simultaneously. Furthermore, in the Preparation Method I, the porous particles to be bound to and reacted with a sulfated polysaccharide also can be sulfated. In the present invention, the preferred sulfated porous particles are sulfated cellulose or agarose particles.

The sulfated polysaccharides are polysaccharides obtained by sulfating at a moiety of hydroxyl group in polysaccharides, and there is no particular limit on the type of the polysaccharides and the sulfation method.

The sulfated polysaccharides used in Preparation Method I has no particular limit as long as it have reductive end and can be adjusted to specified viscosity. The sulfated polysaccharides can be obtained by sulfating, for example, cellulose, dextran, pullulan, gellan and curdlan. The polysaccharides obtained by sulfating dextran or cellulose of low cost and having easily adjustable viscosity are particularly preferred.

In the Preparation Method II, any polysaccharides can be used as long as it is inexpensive and can be adjusted to a specified viscosity. In view of low cost and the applicability of safe water solvent, high water-soluble polysaccharide is more preferred, and thus dextran or pullulan is particularly preferred.

Furthermore, in Preparation Method I, the sulfated polysaccharides useful in Binding Reaction 2B can be any type. In view of low cost, a polysaccharide obtained by sulfating dextran, pullulan, and cellulose is particularly preferred.

Moreover, the source of cellulose has no particular limit, and any cellulose from cotton, pulp, or acetic acid bacteria fermentation can be used in the present invention. Dextran used can be derived from lactic acid bacteria fermentation, and pullulan used can be derived from black yeast. Furthermore, polysaccharides with improved degree of purification, or polysaccharides which are hydrolyzed by sulfuric acid to have low molecular weight also can be used.

Sulfation of polysaccharides can be achieved by a generally known method in which chlorosulfonic acid is used as sulfating agents in a solvent such as dimethyl formamide or pyridine, as described in, for example, U.S. Pat. No. 4,480,091 or Japanese Patent Publication No. 2006-274245.

Especially, in synthesizing low-viscosity sulfated cellulose, a method described in Paragraph No. 0026-0028 in Japanese Patent Publication No. 2006-274245 is preferably used, in which cellulose is swelled in solvents such as pyridine, dimethyl sulfoxide, or dimethyl formamide, and then sulfating agents such as chlorosulfonic acid, piperidine-N-sulfuric acid, anhydrous sulfuric acid-dimethyl formamide complex, sulfur trioxide-pyridine complex, sulfur trioxide-trimethylamine complex, or sulfuric acid-trimethylamine complex is dropped.

In this case, the amount of the sulfating agents used varies with the sulfation rate (sulfur content) of the target sulfated polysaccharide and reaction conditions, and is preferably 1.2-3 equivalents with respect to 1 equivalent hydroxyl group in polysaccharide. The reaction time also varies with the species of the solvent and the sulfating agent, and is preferably 0.5-24 hr, and preferably 0.5-24 hr under an inert atmosphere at preferably 0-100° C., and more preferably 20-85° C.

After the reaction, methanol, ethanol, isopropanol, or acetone is added to the reaction solution, to precipitate the sulfated polysaccharides thus prepared. Alternatively, the sulfated polysaccharides are precipitated by dropping the reaction solution into methanol, ethanol, isopropanol, or acetone.

Additionally, the reaction is stopped by adding distilled water to the reaction solution, and then the reaction solution is neutralized with an alkali such as sodium hydroxide; next, the resulting reaction solution is filtrated or centrifuged, and then the solid component is dissolved into distilled water; afterwards, ethanol, isopropanol, or acetone is added to the solution, to precipitate the sulfated polysaccharide, or, the sulfated polysaccharide is precipitated by dropping the reaction solution into ethanol, isopropanol, or acetone.

The sulfated polysaccharides thus precipitated are recovered and dried, to obtain the sulfated polysaccharides used in the present invention.

The sulfated polysaccharides can be prepared by the method described above, or be commercially available in market. Example of commercially available cellulose sulfate includes, for example, Cellulose Sulfate (trade name, high viscosity type) sold by Kanto Chemical Company and manufactured by Acros Company or dextran sulfate sodium sold by Wako Pure Chemical Industries Ltd.

As described above, the introduction efficiency of sulfate group to the surface of the porous particles will be influenced by the pore size of the porous particles, the molecular weight of the polysaccharides or sulfated polysaccharides, or the viscosity or limiting viscosity depending on the molecular weight. In the present invention, porous particles have an exclusion limit molecular weight of 6000 Da or less when pure water is used as mobile phase and standard polyethylene glycol is used. For the porous particles, the preferred polysaccharides or sulfated polysaccharides preferably has a molecular weight of, or higher than the exclusion limit molecular weight of the porous particles. The viscosity of the sulfated polysaccharides used in Binding Reaction 1 (the viscosity of an aqueous sulfated polysaccharide solution of 1 wt %) has no particular limit, and is preferably in the range of 15-300 Mpa/sec at 20° C. when the sulfated polysaccharides are cellulose sulfate. Moreover, the viscosity of the polysaccharides or sulfated polysaccharides used in Binding Reaction 2 also has no particular limit, and the limiting viscosity is preferably in the range of 0.21-0.90 dL/g, and more preferably in the range of 0.40-0.90 dL/g. If the viscosity (the viscosity of an aqueous sulfated polysaccharide solution of 1 wt %) or limiting viscosity is in the range above, the polysaccharides or sulfated polysaccharides can be arranged on the surface of the porous particles with high efficiency, and thus sulfate group required for binding the virus particles can be introduced to the surface of the particles with high efficiency.

The viscosity of the sulfated polysaccharides used in Binding Reaction 1 can be measured with a single rotating cylinder viscometer according to JIS Z 8803 "Fluid Viscosity—Measurement Methods". The viscosity resistance torque applied to the disc of model B viscometer (Told Sangyo Co., Ltd.) by 1 wt % solution of sulfated polysaccharide in pure water is determined at 20° C., to obtain the viscosity of the aqueous solution.

Moreover, the limiting viscosity of the polysaccharides and sulfated polysaccharides used in Binding Reaction 2 can be calculated by obtaining the viscosity of numerous polymer solutions of different concentrations according to Viscosity Measurement Methods-No. 1 "Capillary Viscometer Method" in General Measurement Methods described in the Japanese Pharmacopoeia ($14^{th}$ Edition), determining the concentration dependence of the viscosity, and then extrapolating the concentration of the resulting straight line to 0. In the present invention, the limiting viscosity is a value calculated according to Viscosity Measurement Methods-No. 1 "Capillary Viscometer Method" in General Measurement Methods described in the Japanese Pharmacopoeia ($14^{th}$ Edition).

Furthermore, it is known that the relationship between the limiting viscosity and the weight average molecular weight of dextran meets the formula below, and thus the limiting viscosity of dextran can be calculated according to the weight average molecular weight:

$$\text{Limiting viscosity}(\eta)=9\times10^{-4}\times\text{weight average molecular weight}(Mw)^{0.5}$$

With the weight average molecular weight as an index, the weight average molecular weight of the polysaccharides or sulfated polysaccharides used in the present invention is preferably 70 kDa or more, and more preferably 150 kDa or more. Moreover, the weight average molecular weight of the polysaccharide or sulfated polysaccharides is most preferably 500 kDa or less.

In the present invention, the sulfur content in the sulfated polysaccharides binding to the porous particles has no particular limit. In Preparation Method I, as the binding is accomplished in cheap alkaline water system, the higher the water solubility of the sulfated polysaccharide is, the more easily the binding is. When a polysaccharide hardly soluble in water such as cellulose is used, it is required to sulfate 15 wt % or above of the polysaccharide, to dissolve the polysaccharide in water easily. Moreover, because the sulfate group introduced into the hydroxyl in the polysaccharide functions as the ligand of the chromatography medium in the present invention, a target such as virus particles can be efficiently adsorbed by increasing the ligand density. Therefore, by increasing the sulfate group as ligand, the adsorption of nucleic acid derived from host cells and oppositely negatively charged can also be decreased due to electric repulsion. Preferably, one sulfate group is introduced into each glycoseforming the polysaccharide. Therefore, in view of the operability and performance of the binding reaction, the sulfur content is preferably 12 wt % or more, and more preferably 15 wt % or more. In this case, in view of the adsorption capability, the sulfur content is preferably in the range of 0.2-6 wt % with respect to the finished product of the present invention prepared by binding the polysaccharides to the porous particles.

In Preparation Method II, the adsorption performance of the chromatography medium can be improved by introducing a quantity of sulfate groups. However, introduction of too many sulfate groups will cause the medium to be softened in the case that the porous particles are sulfated. Therefore, in view of the fluidity property in practical use, the sulfur content is preferably in the range of 0.2-6 wt % with respect to the chromatography medium of the present invention.

The sulfur content in the sulfated polysaccharides can be calculated by ion chromatography. The specific determination conditions are as described in the following embodiments.

In the present invention, the sulfated polysaccharides can also be in the form of salt. For example, especially in the case of cellulose sulfate, sodium or potassium salt is preferred in view of the preservation stability and the low production cost.

While the chromatography medium of the present invention can be specifically prepared by Preparation Method I or Preparation Method II, the cost of Preparation Method II is lower than Preparation Method I, as the sulfated polysaccharides are more expensive due to low binding rate on the porous particles. Moreover, in Preparation Method II, when the porous particles are polysaccharides, the sulfate group can also be introduced into the particles, and thus chromatography medium having widely or densely distributed ligands can be easily obtained.

The specific aspect of the Preparation Method II has no particular limit, and in the present invention, an aspect having the following two steps is preferred.

Step 1: porous particles and polysaccharides are cross-linked by using cross-linking agents having two or more functional groups, to obtain polysaccharide-binding porous particles.

Step 2: The polysaccharide-binding porous particles obtained in step 1 are sulfated with sulfating agents.

The chromatography medium of the present invention contains the sulfated polysaccharides, thus being suitable for adsorbing and recovering enveloped virus such as influenza virus, HIV, Japanese Encephalitis virus, hepatitis virus.

The adsorption of the chromatography medium of the present invention for influenza virus can be evaluated according to, for example, the method described in Japanese Patent Publication No. 1986-47168 or European Patent Application Publication No. 1808697. The evaluated influenza virus can be A or B type, and can be derived from incubated egg or cultured cells such as MDCK cell or have been inactivated with formalin or β-propiolactone or not. However, in order to improve the purification level and the recovery rate, the solution of influenza virus is preferably pretreated by, for example, filtration or removal of nucleic acid.

It is very important to remove nucleic acid derived from host cells in the vaccine preparation. Generally, nucleic acid is negatively charged due to its structure, thus electrically repulses the sulfate group as the ligand of the chromatography medium of the present invention. Accordingly, the nonspecific adsorption of nucleic acid derived from host cells on the chromatography medium of the present invention can be effectively decreased by increasing the ligand density. For this purpose, the effective sulfur content is preferably 0.2 wt % or more.

The influenza virus adsorbed on the chromatography medium of the present invention can be eluted and recovered as ion exchange mode using a high-content salt solution of, for example, NaCl. The recovered influenza virus can be evaluated by hemagglutinin titer (HA) according to a commonly known method such as red cell agglutination test. The virus evaluation method is described in, for example, Classified Theory on Virus Experiment (Revised $2^{nd}$ Edition) edited by National Institute of Health Alumni Association (Maruzen).

Purification of influenza virus by chromatography is well known in this field, and described in, for example, Japanese Patent Publication No. 1988-47186 or European Patent Application Publication No. 1,808,697. As shown in FIG. 1, the chromatography medium of the present invention can also be used to purify any influenza virus amplified with egg or cultured cell as host, according to the same method as described in Japanese Patent Publication No. 1986-47186 or European Patent Application Publication No. 1,808,697.

As desired, a step of removing a salt or impurities such as nucleic acid or protein derived from the host can also be included, especially for adsorbing influenza virus on the chromatography medium of the present invention with high efficiency. This can be achieved according to a well known method for purifying protein with a common chromatography.

Furthermore, the method for preparing influenza virus into vaccine is well known from International Publication Nos. 01/21151 or 02/28422. The chromatography medium of the present invention can also be used in purification of the protein containing hemagglutinin of the influenza virus obtained in the manner described above. For example, an ether or surfactant is used to destroy the virus particles in the purified virus solution obtained in step of FIG. 1. The vaccine component can be purified from the dissolved portion with a common chromatograph by using chromatography medium of the present invention according to a well known method.

EMBODIMENTS

Hereinafter, the present invention is further described in detail with reference to the following embodiments, but the present invention is not limited thereto. Furthermore, "%" denotes "wt %", unless specifically indicated.

1. Determination Method

The determination methods used in Embodiments are as described below.

<Exclusion Limit Molecular Weight>
Determination of Gel Partition Coefficient Kav
(1) Instrument and Reagent
Column: Empty column ¼×4.0 mm
I.D.×300 mm, 10 F (Tosoh)
Reservoir: Packe•⅜ (Tosoh)
Pump: POMP P-500 (Pharmacia)
Pressure Meter: AP-53A (KEYENCE)
(2) Column Packing Method The column and the reservoir were connected, and an end fitting is connected at the bottom of the column. 15 g wet gel formed by filtering the gel for Kav determination under vacuum was taken and weighed, and placed in a 50 mL beaker. Into the breaker, 20 mL extra pure water was added slowly along the wall of the reservoir and stirred gently, to disperse the gel into the extra pure water. The gel remained in the beaker was washed with a small amount of extra pure, and then slowly added into the column. Next, extra pure water was added just to a level reaching to the head of the reservoir, and then the reservoir was covered with a lid. An adapter was connected to the top of the reservoir, for transporting extra pure water with a pump. A pressure meter was disposed in the liquid feeding pipeline in advance to monitor the pressure. The flow rate was raised until the pressure reached to 0.3 MPa, and then the extra pure water was flowed through for 30 min while packing. After packing, the pump was closed, and the adapter and the lid of the reservoir were removed. Afterwards, the reservoir was removed after the extra pure water was sucked out with a pipette, the gel exposed from the column was removed, and the column was connected to an end fitting.

(3) Kav Determination Device
System: SCL-10APVP (SHIMAZU)
Workstation: CLASS-VP (SHIMAZU)
Refractive Index Detector: RID-10A (SHIMAZU)
Pump: LC-10AT (SHIMAZU)
Auto-injector: SIL-10ADVP (SHIMAZU)
(4) Test Sample for Kav Measurement
1. PEG-19000 (SCIENTIFIC POLYMER PRODUCTS) having a molecular weight of 19700
2. PEG-8650 (POLYMER LABORATORIES) having a molecular weight of 8650
3. PEG-4120 (POLYMERLABORATORIES) having a molecular weight of 4120
4. PEG-590 (POLYMERLABORATORIES) having a molecular weight of 590
5. PEG-220 (POLYMERLABORATORIES) having a molecular weight of 220
(5) Calculation Equation of Kav $$Kav = (Ve - V_0)/(Vt - V_0)$$

[in which, Ve is the retention volume of the sample (mL), Vt is the volume of the empty column (mL), and $V_0$ is the retention volume of dextranT2000 (mL)].

(6) Determination Result

Figure 2:
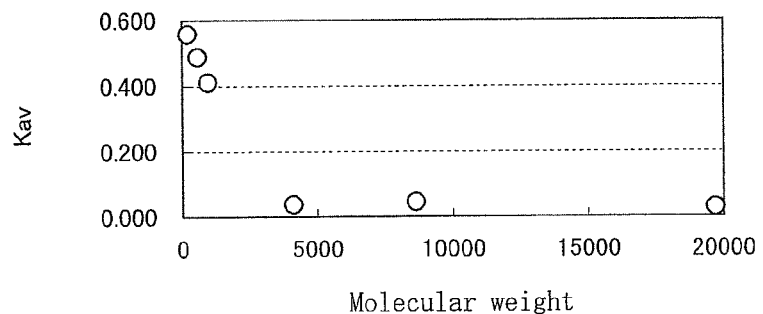
FIG. 2 is a diagram showing a relationship between Kav of standard polyethylene glycol and commercially available cellulose particles GH25.

The determination result for the gel partition coefficient Kav of the porous particles GH25 used in this embodiment is shown in FIG. 2. It can be known from the result in FIG. 2 that, the exclusion limit molecular weight of GH25 used in the present invention is 3000 Da where standard polyethylene glycol is used.

<Average Particle Size>

Wet cellulose particles were taken and placed on a slide glass, and long diameters of any 200 particles from photos taken by using an optical microscope at a magnification of 100× were determined, then a mean value of the measured long diameters was calculated and used as average particle size.

<Viscosity>

The viscosity was determined with a single rotating cylinder viscometer according to JIS Z 8803 "Fluid Viscosity—Measurement Methods". That is, the viscosity resistance torque applied to the disc of model B viscometer (Toki Sangyo Co., Ltd.) by 1 wt % solution of cellulose sulfate in pure water was determined at 20° C., to obtain the viscosity of the aqueous solution.

<Limiting Viscosity>

The limiting viscosity of the polysaccharide was determined by obtaining the viscosity of numerous polymer solutions of different concentrations according to Viscosity Measurement Methods-No. 1 "Capillary Viscometer Method" in General Measurement Methods described in the Japanese Pharmacopoeia (14$^{th}$ Edition), determining the concentration dependence of the viscosity, and then extrapolating the concentration of the resulting straight line to 0.

<Sulfur Content>

The sulfur content was measured by ion chromatography and calculated by using the method described below. A sample dried in vacuum for 16-20 h at 60° C. was ground in a mortar, and then dried for 2 hr at 105° C. 0.05 g of the dried sample was added into 2.5 ml of 2 M hydrochloric acid, and hydrolyzed for 16 hr at 110° C. After cooling in an ice bath, 1 ml supernatant was neutralized with 2 M aqueous sodium hydroxide solution, and then fixed at a volume of 25 ml. At an oven temperature of 40° C., with ICS-A-23 manufactured by Yokogawa Co., Ltd as column, 3 mM $Na_2CO_3$ solution and 15 mM sulfuric acid at a flow rate of 1 ml/min as eluant and stripping solution respectively, IC7000 ion chromato analyzer manufactured by Yokogawa Co., Ltd. was used for analysis, and the $SO_4$ concentration was calculated from the standard curve plotted with the standard solutions below. The blank value is that obtained without adding the dried sample. 2 μg/ml standard $SO_4$ solution (manufactured by Kanto Chemical Company, mixed anion standard solution IV) was used as standard solution in this determination, diluted in series, and analyzed by an ion chromato analyzer under the same conditions, to plot a standard curve. The sulfur content was calculated according to an equation below. Furthermore, $X_{sample}$, and $X_{blank}$ are concentrations calculated from the standard curve plotted with standard $SO_4$ solution (×10$^{-4}$%).

$$\text{Sulfur content}(\times 10^{4}\%) = (X_{sample} - X_{blank}) \times 25 \times 2.5 \times 0.3333/0.05$$

<Amount of Eluted Lysozyme>

The chromatography medium was suspended into an adsorption buffer (0.01 M phosphate buffer, containing 0.15 M NaCl, pH 7.0), after reaching to equilibrium, 2 mL suspension was packed in a column having an inner diameter of 0.5 cm, through which 40 mL buffer above was flowed at 40 mL/h. Next, 30 mL of 3.33 mg/mL lysozyme (manufactured by Seikagaku Co., Ltd.) solution in the adsorption buffer as solvent was circularly flowed through the packed column for 1 hr at a flow rate of 60 mL/h. Then, the column was washed with 20 mL adsorption buffer. Next, 50 mL elution buffer (0.01 M phosphate buffer, containing 0.6 M NaCl, pH 7.0) at 50 mL/h was used to elute out the lysozyme. The absorbency (A) at 280 nm of eluted lysozyme (50 ml) was determined with the elution buffer as a control. The standard solution was obtained by diluting the lysozyme solution 10 times with the elution buffer.

Amount of eluted lysozyme(mg/mL-gel)=0.333×25×
(absorbency at 280 nm of the eluted lysozyme solution/absorbency at 280 nm of the standard solution)

<HA Titer>

50 μL physiological saline was added to a round-bottom 96 well (8 rows×12 columns) plate, 50 μL sample was added to the first well and mixed to dilute the sample 2 times, and then 50 μL the diluted solution was added to the next well and fully mixed. 2 times-diluted series solutions were similarly prepared till the 12$^{th}$ well. The control was obtained by adding physiological saline alone to the 1$^{st}$ to 12$^{th}$ wells. 50 μL of 0.5% chicken red blood cell suspension was added to the sample and control and mixed, the mixture was stood at room temperature for 30 min, and then the state of aggregation of the red blood cell was determined. The red blood cell precipitated at the bottom that can easily flow is judged to be aggregation negative, and that will not flow is judged to be aggregation positive, and the maximum dilution of the virus exhibiting aggregation negative was deemed as HA titer.

<Fluidity Property>

In a column of inner diameter 2.2 cm×height 20 cm made of polycarbonate (manufactured by Tokyo Rikakikai Co., Ltd.), the chromatography medium was packed to a height of 20 cm. Pure water at 24° C. was flowed through the column, and then the inlet and outlet pressures of the column were measured. Furthermore, in the initial stage of flowing, the flow started from a flow rate of 20 mL/min or below, and then the flow rate was increased stepwise, and the pressure was measured after 3 to 5 min of continuous flowing. The pressure is calculated by subtracting the pressure at the outlet of the column from the pressure at the inlet of the column. The linear velocity is calculated according to the equation below.

Linear velocity(cm/hr)=Flow rate in measurement (mL/hr)/Sectional area of column($cm^2$)

<Epoxide Group Content>

Epoxide group content was determined according to the method described in Japanese Patent Publication 2000-321267. First, about 10 g test gel was washed for 15 min with 500 ml pure water, and then suction-filtered to fully remove water, to obtain the test sample. About 1 g sample was first determined for water content with an IR moisture meter. Next, 1.00 g test sample was each placed in 3 capped conical flasks of 50 ml. Into the conical flasks, 3 ml of 1.3 M sodium thiosulfate was added, and then oscillated at 30° C. for 1 hr. Afterwards, 1-2 drops of phenolphthalein solution was added into the conical flasks, and titrated with 0.01 M hydrochloric acid, to calculate the epoxide group content.

$$\text{Epoxide group content}(\mu\text{mol/g-wet})=0.01\times f\times A\times 10^3$$

F: Hydrochloric acid factor a: Titration volume of 0.01 M hydrochloric acid (ml)

Epoxide group content(μmol/g-dry)=Epoxide group content(μmol/g-wet)×water content <Determination of 10% DBC with HA Titer as Index>

Each trial-produced chromatography medium was dispersed in water, and degassed with stirring under vacuum. Then, a column of Φ3×50 mm was packed with the chromatography medium, and mounted on a Biologic LP System (manufactured by Bio-Rad Co., Ltd.). Next, 0.01 M phosphate buffer (pH 7.4) of 10 times of the column volume or above was flowed through the column to make the column to be equilibrated. Afterwards, 11 mL test virus solution of H7N7 strain filtered by a membrane filter (product name: DISMIC-25cs, manufactured by Advantec Co., Ltd.) made of cellulose acetate was flowed through the column, and at the same time, the effluent from the column was recovered in a unit of 1 mL. HA titer was measured using 50 μL of 1 mL fraction of effluent. Furthermore, amount of total solution (μL) was calculated until the fraction reach 1/10 of the HA titer of 504 test virus solution. 10% DBC in this system of measurement is calculated according to the equation below.

10% DBC(HA titer/ml-gel)=(amount of total solution×1/50×HA titer of test virus solution)/column volume(ml-gel)

2. Preparation of Test Influenza Virus

A/PR/8/1934 (H1N1) strain and A/duck/Hokkaido/Vac-2/04 (H7N7) strain were selected as seed viruses, and the individual stock solution of the preserved virus was diluted 1000 times with the sterilized bouillon medium (manufactured by Nissui Pharmaceutical Co., Ltd., containing 1000 U/mL of penicillin and 1 mg/mL of streptomycin), to obtain two kinds of diluted virus solutions for inoculation.

For each of the H1N1 and H7N7 virus strains, the diluted virus solution was intraperitoneally inoculated in an incubated egg of 10 days, incubated for 2 days at 37° C., and then stood for 16 hr at 4° C. The chorioallantoic liquids were recovered from the egg, inactivated by adding 0.1% β-propiolactone, and formulated into two kinds of test virus solutions. 1 lot of H1N1 strain, and 3 lots of H7N7 strain having different HA titer per unit of volume were prepared separately, and used in virus adsorption test in this embodiment.

3. Preparation of Chromatography Medium

<Binding Reaction 1>

(1) Synthesis of Sulfated Polysaccharide A 180 g crystalline cellulose (Ceolus PH-101 (trade name), having an average polymerization degree of 242) and 160 mL N,N-dimethyl formamide were added into a 3 L separable flask (reactor) equipped with a thermometer, a dropping funnel, a stirrer, and a nitrogen introduction pipe, and stirred overnight. Next, 1221 g 18%-anhydrous sulfuric acid-DMF complex was added over 35 min while cooling in an ice bath, and then reacted for 6 hr at 20° C. after being warmed in a thermostat bath of 20° C. for 20 min.

After the reaction, while cooling in an ice bath until the temperature of the reaction solution reached to 5° C., 1220 mL extra pure water was slowly added over 75 min, and then 1 N sodium hydroxide solution was slowly added till the pH value of the reaction solution reached to 7. The resulting precipitate was filtered, and then the filtrate was added to 20 L isopropanol, to obtain a precipitate. Then, the precipitate was filtered, and dried for 8 hr under vacuum at 40° C., to obtain sodium cellulose sulfate (sulfated polysaccharide A). The yield of the resulting sodium cellulose sulfate is 130 g, the solubility in pure water at 20° C. is 15 g/L, the sulfur content is 14.0%, and the viscosity is 18.4 mPa·s.

(2) Synthesis of Sulfated Polysaccharide B 5.0 g absorbent cotton standardized by Japanese Pharmacopoeia and 350 mL N,N-dimethyl formamide (DMF) were added to a 2 L separable flask (reactor) equipped with a thermometer, a dropping funnel, a stirrer, and a nitrogen inlet, and stirred overnight, to fully infiltrate the absorbent cotton by DMF. Next, the reactor was placed in a thermostat bath of 10° C., and 123 g 18%-anhydrous sulfuric acid-DMF complex was added over 1 hr, and then reacted for 4 days while being warmed by the thermostat bath of 10° C.

After the reaction, 1000 mL water was slowly added over 75 min, and then 1 N sodium hydroxide solution was slowly added till pH 7, while the reaction solution was cooled in an ice bath until the temperature of the reaction solution reached to 5° C. The resulting precipitate was filtered, and then the filtrate was added to 1000 mL isopropanol, to obtain a precipitate. Then, the precipitate was filtered, and dried for 8 hr under vacuum at 40° C., to obtain sodium cellulose sulfate (sulfated polysaccharide B). The yield of the resulting sodium cellulose sulfate is 13 g, the sulfur content is 16.0%, and the viscosity is 45.7 mPa·s.

(3) Preparation Example 1

Binding of Porous Particles with Sulfated Polysaccharides

1) Epoxidation of Porous Particles

Cellufine GH25 (cellulose particles manufactured by Chisso Corp.) was used as the raw material porous particles. The particle size of the porous particles is 44-105 µm, and the average particle size is 67 µm. Furthermore, the exclusion limit molecular weight is calculated to be about 3000 Da according to the relationship between the standard polyethylene glycol and Kay as shown in FIG. 2.

750 g Cellufine GH25 (water content of 2.89) and 6415 mL water were added together to a reactor equipped with a stirrer. 1344 g of 20% aqueous NaOH solution was added at an adjusted internal temperature of 30° C. with fully stirring. After stirring for 1 hr, 1482 g epichlorohydrin was added and reacted for 2 hr. After the reaction, the reaction solution was filtered, and the residue was thoroughly washed with water, until the filtrate reached to pH 7. After 30 min of suction-drying, 757 g epoxided porous particles (epoxide-activated wet gel) were obtained. 1.0 g epoxide-activated wet gel and 3.0 mL of 1.3 M sodium thiosulfate solution were oscillated for 1 h in an oscillator of 30° C., and then titrated with 0.1 mol·L hydrochloric acid, thereby quantifying epoxide group. The epoxide group content is 308.6 mol/g (dry).

2) Amination of Epoxide-Activated Wet Gel 650 g epoxide-activated wet gel prepared above and 975 mL of 25% aqueous ammonia were added together to a reactor equipped with a stirrer, and reacted for 2 hr at an adjusted inner temperature of 35-40° C. with fully stirring. After the reaction, the reaction solution was filtered, and the residue was thoroughly washed with water, until the filtrate was neutral. After 30 min of suction-drying, 653 g aminated epoxide-activated wet gel (aminated wet gel) was obtained. The water content in the aminated wet gel is calculated to be 3.28% by the weight reduction of the particles dried overnight in a suction-drier at 50° C. Furthermore, the nitrogen content is calculated to be 4500 ppm by using the Kjeldahl method.

3) Binding of Sulfated Polysaccharides A 80 g aminated wet gel and 160 mL of 0.02 M phosphate buffer (pH 7.0) were added together to a reactor equipped with a stirrer, and stirred for 1 hr at an adjusted inner temperature of 50° C. Then, 0.61 g sulfated polysaccharides A was added and reacted for 48 hr at 50° C. Afterwards, 2.44 g dimethyl aminoborane were added, reacted for 72 h, and the reaction solution was filtered. The residual white solid was thoroughly washed with water and suction-dried for 15 min, to obtain 80 g sulfated polysaccharide-binding wet gel.

4) Protection of Amino Residue 80 g sulfated polysaccharides-binding wet gel and 400 mL of 5.3 mol/L sodium acetate solution were added together to a reactor equipped with a stirrer. 100 mL acetic anhydride was added dropwise, and then reacted for 30 min at an adjusted inner temperature of 0° C. with fully stirring. An additional 100 mL acetic anhydride was further added dropwise and reacted for 30 min after the inner temperature was raised to room temperature. After the reaction, the reaction solution was filtered, and the residue was thoroughly washed with water, until the filtrate was neutral. After 15 min of suction-drying, 77 g chromatography medium was obtained. The sulfur content in the dried gel is 0.23%, and the eluting amount of lysozyme is 0.9 mg/mL-gel.

(4) Preparation Example 2

Binding of Porous Particles and Sulfated Polysaccharides

1) Binding of Sulfated Polysaccharides B 12 g aminated wet gel obtained in Preparation Example 1 and 24 mL of 0.02 M phosphate buffer (having a pH value of 7.0) were added together to a reactor equipped with a stirrer. 0.421 g sulfated polysaccharides B was added and reacted for 48 h at 50° C. after adjusting the inner temperature to 50° C. and stirring for 1 hr. 0.42 g dimethyl aminoborane was added, reacted for 72 hr, and the reaction solution was filtered. The residual white solid was thoroughly washed with water and suction-dried for 15 min, to obtain 12.5 g sulfated polysaccharides-binding wet gel.

2) Protection of Amino Residue 12.5 g sulfated polysaccharide-binding wet gel and 62.5 mL of 5.3 mol/L sodium acetate solution were added together to a reactor equipped with a stirrer. 15.6 mL acetic anhydride was added dropwise, and then reacted for 30 min at an adjusted inner temperature of 0° C. with fully stirring. An additional 15.6 mL acetic anhydride was further added dropwise and reacted for 30 min after the inner temperature was raised to room temperature. After the reaction, the reaction solution was filtered, and the residual white solid was thoroughly washed with water. After 15 min of suction drying, 12.0 g chromatography medium was obtained. The sulfur content of the dried gel is 0.13%, and the eluting amount of lysozyme is 1.8 mg/mL-gel.

(5) Preparation Example 3

Binding of Porous Particles and Sulfated Polysaccharide

1) Binding of Cellulose Sulfate Manufactured by Acros Corp.

20 g aminated wet gel obtained in Preparation Example 1 and 40 mL of 0.02 M phosphate buffer (having a pH value of 7.0) were added together to a reactor equipped with a stirrer. 2.11 g commercially available cellulose sulfate (manufactured by Acros Corp., having a viscosity of 241.0 mPa·s) was added, and then reacted for 48 hr at 50° C. after adjusting the inner temperature to 50° C. and stirring for 1 hr. 0.7 g dimethyl aminoborane was added, reacted for 72 h, and then the reaction solution was filtered. The residual white solid was thoroughly washed with water and then suction-dried for 15 min, to obtain 18.5 g sulfated polysaccharide-binding wet gel.

2) Protection of Amino Residue 18.5 g sulfated polysaccharide-binding wet gel and 62.5 mL of 5.3 mol/L sodium acetate solution were added together to a reactor equipped with a stirrer. 23 mL acetic anhydride was added dropwise, and then reacted for 30 min at an adjusted inner temperature of 0° C. with fully stirring. An additional 23 mL acetic anhydride was further added dropwise and reacted for 30 min after the inner temperature was raised to room temperature. After the reaction, the reaction solution was filtered, and the residual was thoroughly washed with water, until the filtrate was neutral. 18.4 g chromatography medium was obtained after 15 min of suction-drying. The sulfur content of the dried gel is 0.23%, and the eluting amount of lysozyme is 2.8 mg/mL-gel.

(6) Preparation Example 4

Binding of Porous Particles and Sulfated Polysaccharide

1) Binding of Cellulose Sulfate Manufactured by Acros Corp.

80.0 g aminated wet gel obtained in Preparation Example 1 and 160 mL of 0.02 M phosphate buffer (having a pH value of 7.0) were added together to a reactor equipped with a stirrer. 7.0 g commercially available cellulose sulfate (manufactured by Acros Corp., having a viscosity of 241.0 mPa·s) was added, and then reacted for 48 hr at 50° C. after adjusting the inner temperature to 50° C. and stirring for 1 hr. 2.8 g dimethyl aminoborane was added, reacted for 72 hr, and then the reaction solution was filtered. The residual white solid was thoroughly washed with water and then suction-dried for 15 min, to obtain 83.3 g sulfated polysaccharides-binding wet gel.

2) Protection of Amino Residue 83.3 g sulfated polysaccharides-binding wet gel and 416 mL of 5.3 mol/L sodium acetate solution were added together to a reactor equipped with a stirrer. 104 mL acetic anhydride was added dropwise, and then reacted for 30 min at an adjusted inner temperature of 0° C. with fully stirring. An additional 104 mL acetic anhydride was further added dropwise and reacted for 30 min after the inner temperature was raised to room temperature. After the reaction, the reaction solution was filtered, and the residual was thoroughly washed with water, until the filtrate was neutral. 83.3 g chromatography medium was obtained after 15 min of suction drying. The sulfur content of the dried gel is 0.03%.

4. Virus Adsorption Test 1

(1) Comparison of chromatography medium of Preparation Example 1 with chromatography medium of Preparation Example 3

The chromatography medium of Preparation Example 1 and Preparation Example 3 were used as medium.

Each medium was dispersed in water, and degassed with stirring under vacuum. Then, a column of Φ3×50 mm was packed with the chromatography medium, and mounted on a Biologic LP System (manufactured by Bio-Rad Co., Ltd.). Next, 0.01 M phosphate buffer (pH 7.4) of 10 times of the column volume or above was flowed through to make the column to be equilibrated. Afterwards, 8 mL test virus solution of H7N7 strain (having a total HA titer in use of 40960) filtered by a membrane filter (product name: DISMIC-25cs, manufactured by Advantec Co., Ltd.) made of cellulose acetate was flowed through the column, and at the same time, the effluent from the column was recovered in a unit of 1 mL After the flowing of the test virus solution, 0.01 M phosphate buffer –0.19M NaCl (pH 7.2) was flowed to wash off the non-adsorbed portion. Then, 0.01 M phosphate buffer –3M NaCl (pH 7.0) was flowed until the virus adsorbed on the column was completely eluted. Afterwards, the HA titer of the recovered effluent was measured, to calculate the adsorbed amount. The result shows that the adsorbed amount of virus is 21000 HA/mL-gel when the chromatography medium of Preparation Example 1 is used, and is 25720 HA/mL-gel when the chromatography medium of Preparation Example 3 is used. The adsorbed amount (HA titer) was calculated by the equation below.

Adsorbed amount=Total HA titer of the flowed liquid−Total HA titer of the non-adsorbed portion (2) Comparison of chromatography medium of Preparation Example 3 with Commercially Available Cellufine Sulfate The chromatography medium of Preparation Example 3 and commercially available Cellufine Sulfate (Chisso Corp., having a sulfur content of 0.09%) were used as packing material. This test was performed following the virus adsorption test described above, except that the test virus was H1N1 strain, and the volume of the test virus solution was set to be 2 mL (having a total HA titer in use of 81920). The result shows that the adsorbed amount of the virus is 64840 HA/mL-gel when the chromatography medium of Preparation Example 3 is used, and the adsorption property is comparable to the 64800 HA/mL-gel when commercially available Cellufine Sulfate (Chisso Corp.) is used.

5. Comparison of Fluidity Property

The fluidity properties of Cellufine Sulfate and the chromatography medium of Preparation Example 4 having substantially the same sulfur content were compared.

According to the test method described above, the fluidity property of the chromatography medium (having a sulfur content in dry gel of 0.03%) obtained in Preparation Example 4 was determined. The fluidity property is linear velocity 2200 cm/h when the value obtained by subtracting the pressure at the outlet of the column from the pressure at the inlet of the column reaches to 0.3 MPa. On the other hand, the fluidity property of the cellulose particles obtained by directly sulfating in a manner such that the sulfur content in dry gel is 0.02% with respect to Cellufine GH25 is linear velocity 700 cm/h under the same conditions. With the same sulfur content, the chromatography medium prepared in the present invention exhibits an about 3 times improved fluidity property. Furthermore, the gel having a sulfation rate of 0.02% was prepared as follows.

The air in a 500 ml separable flask equipped with a dropping funnel, a cooler condenser, a stirrer, and a thermometer was fully replaced with nitrogen, and 295 g dehydrated pyridine was added to the reactor, sealed with nitrogen, and then cooled to 5° C. Next, 3.00 g chlorosulfonic acid was added dropwise over 5 min through the dropping funnel, and the temperature in the reactor was raised to 65° C.±2° C. after stirring at 5° C.-10° C. for 1 hr. Afterwards, 45 g (dry weight) GH25 (having a water content of 0.38%) previously dried to a water content of 1% or less under reduced pressure of 13 Pa at 80° C. by using a vacuum drier was added to the reactor, and reacted for 4 hr. Then, the temperature in the reactor was cooled to 25° C., 43.6 g of 20% aqueous sodium hydroxide solution was added and stirred for 30 min, and then the reaction was stopped. After standing overnight, the reaction solution was filtered, and the residue was thoroughly washed with water, until the filtrate was neutral. After 15 min of suction-drying, 110 g of the chromatography medium (having a sulfur content in the dried gel of 0.02%) was obtained.

The test results are summarized in Table 1. The chromatography medium of Preparation Example 3 exhibits an adsorption performance comparable to that of the commercially available sulfated Cellufine. Moreover, with the same sulfur content, the chromatography medium prepared in the present invention exhibits an about 3 times improved fluidity property of that of the commercially available sulfated Cellufine. Therefore, the cellulose particles with cellulose sulfate of the present invention as ligand can efficiently adsorb virus and can be used at high flow rate.

TABLE 1

| Chromatography medium | Sulfated Polysaccharides | Viscosity MPa · s | Sulfur Content % | Adsorbed Amount of Lysozyme mg/mL-gel | Adsorbed Amount of H7N7 Virus HA/mL-gel |
|---|---|---|---|---|---|
| Preparation Example 1 | A | 18.4 | 0.2 | 0.9 | 21000 |
| Preparation Example 2 | B | 45.7 | 0.1 | 1.8 | — |
| Preparation Example 3 | Manufactured by Acros Corp. | 241.0 | 0.2 | 2.8 | 25720 |

6. Preparation of Chromatography Medium <Binding Reaction 2A>

(1) Preparation of Epoxide-activated Wet Gel (Reference Examples 1-3), and Preparation of Complex of the Gel with Polysaccharide (Reference Examples 4-12)

1) Reference Example 1

Cellufine GH25 (cellulose particles manufactured by Chisso Corp.) was used as the raw material porous particles. 850 g Cellufine GH25 (having a water content of 3.68) and 5750 mL pure water were added together to a reactor equipped with a stirrer. 1225 g of 20% aqueous NaOH solution was added at an adjusted internal temperature of 30° C. with fully stirring. After stirring for 1 hr, 1319 g epichlorohydrin was added and reacted for 2 hr. After the reaction, the reaction solution was filtered, and the residue was thoroughly washed with water, until the filtrate was neutral. After 30 minutes of suction-drying, 847 g epoxided porous particles (epoxide-activated wet gel) were obtained. The epoxide group content is 313 μmol/g-dry.

2) Reference Example 2

1000 g Cellufine GH25 (having a water content of 5.38) and 4320 mL pure water were added together to a reactor equipped with a stirrer. 987.5 g of 20% aqueous NaOH solution was added at an adjusted internal temperature of 30° C. with fully stirring. After stirring for 1 hr, 318 g epichlorohydrin was added and reacted for 2 hr. After the reaction, the reaction solution was filtered, and the residue was thoroughly washed with water, until the filtrate was neutral. After 30 minutes of suction-drying, 755 g epoxided porous particles (epoxide-activated wet gel) were obtained. The epoxide group content is 105 mol/g-dry.

3) Reference Example 3

1000 g Cellufine GH25 (having a water content of 5.38) and 4320 mL pure water were added together to a reactor equipped with a stirrer. 987.5 g of 20% aqueous NaOH solution was added at an adjusted internal temperature of 30° C. with fully stirring. After stirring for 1 hr, 106 g epichlorohydrin was added and reacted for 2 hr. After the reaction, the reaction solution was filtered, and the residue was thoroughly washed with water until the filtrate was neutral. After 30 minutes of suction-drying, 720 g epoxided porous particles (epoxide-activated wet gel) were obtained. The epoxide group content is 17.3 μmol/g-dry.

4) Reference Example 4

28.0 g cosmetic pullulan (manufactured by Hayashibara Co., Ltd., having a limiting viscosity of 0.73 dL/g) and 155.5 mL pure water were added together to a reactor equipped with a stirrer, and stirred till pullulan was completely dissolved. 120 g epoxide-activated wet gel (having a water content of 3.61) prepared in Reference Example 1 was added to the reactor. The inner temperature was adjusted to 30° C. with fully stirring. After stirring for 1 hr, 17.3 g of 45% aqueous NaOH solution was added and reacted for 18 hr. After the reaction, the reaction solution was filtered, and the residue was thoroughly washed with water, until the filtrate was neutral. After 30 minutes of suction-drying, 121 g pullulan binding porous particles were obtained.

5) Reference Example 5

44.4 g cosmetic pullulan (manufactured by Hayashibara Co., Ltd., having a limiting viscosity of 0.73 dL/g) and 155.5 mL pure water were added together to a reactor equipped with a stirrer, and stirred till pullulan was completely dissolved. 120 g epoxide-activated wet gel (having a water content of 3.61) prepared in Reference Example 1 was added to the reactor. The inner temperature was adjusted to 30° C. with fully stirring. After stirring for 1 hr, 17.3 g of 45% aqueous NaOH solution was added and reacted for 18 hr. After the reaction, the reaction solution was filtered, and the residue was thoroughly washed with water, until the filtrate was neutral. After 30 minutes of suction-drying, 117 g pullulan binding porous particles were obtained.

6) Reference Example 6

63.0 g cosmetic pullulan (manufactured by Hayashibara Co., Ltd., having a limiting viscosity of 0.73 dL/g) and 155.5 mL pure water were added together to a reactor equipped with a stirrer, and stirred till pullulan was completely dissolved. 120 g epoxide-activated wet gel (having a water content of 3.61) prepared in Reference Example 1 was added to the reactor. The inner temperature was adjusted to 30° C. with fully stirring. After stirring for 1 hr, 17.3 g of 45% aqueous NaOH solution was added and reacted for 18 hr. After the reaction, the reaction solution was filtered, and the residue was thoroughly washed with water, until the filtrate was neutral. After 30 minutes of suction-drying, 116 g pullulan binding porous particles were obtained.

7) Reference Example 7

29.0 g cosmetic pullulan (manufactured by Hayashibara Co., Ltd., having a limiting viscosity of 0.73 dL/g) and 135.8 mL pure water were added together to a reactor equipped with a stirrer, and stirred till pullulan was completely dissolved. 150 g epoxide-activated wet gel (having a water content of 4.31) prepared in Reference Example 2 was added to the reactor. The inner temperature was adjusted to 30° C. with fully stirring. After stirring for 1 hr, 17.9 g of 45% aqueous NaOH solution was added and reacted for 18 hr. After the reaction, the reaction solution was filtered, and the residue was thoroughly washed with water until the filtrate was neutral. After 30 minutes of suction-drying, 147 g pullulan binding porous particles (having a water content of 3.90) were obtained.

8) Reference Example 8

46.0 g cosmetic pullulan (manufactured by Hayashibara Co., Ltd., having a limiting viscosity of 0.73 dL/g) and 135.8 mL pure water were added together to a reactor equipped with a stirrer, and stirred till pullulan was completely dissolved. 150 g epoxide-activated wet gel (having a water content of 4.31) prepared in Reference Example 2 was added to the reactor. The inner temperature was adjusted to 30° C. with fully stirring. After stirring for 1 hr, 17.9 g of 45% aqueous NaOH solution was added and reacted for 18 hr. After the reaction, the reaction solution was filtered, and the residue was thoroughly washed with water, until the filtrate was neutral. After 30 minutes of suction-drying, 145 g pullulan-binding porous particles (having a water content of 4.99) were obtained.

9) Reference Example 9

65.2 g cosmetic pullulan (manufactured by Hayashibara Co., Ltd., having a limiting viscosity of 0.73 dL/g) and 135.8 mL pure water were added together to a reactor equipped with a stirrer, and stirred till pullulan was completely dissolved. 150 g epoxide-activated wet gel (having a water content of 4.31) prepared in Reference Example 2 was added to the reactor. The inner temperature was adjusted to 30° C. with fully stirring. After stirring for 1 hr, 17.9 g of 45% aqueous NaOH solution was added and reacted for 18 hr. After the reaction, the reaction solution was filtered, and the residue was thoroughly washed with water, until the filtrate was neutral. After 30 minutes of suction-drying, 142 g pullulan-binding porous particles (having a water content of 4.83) were obtained.

10) Reference Example 10

54.48 g cosmetic pullulan (manufactured by Hayashibara Co., Ltd., having a limiting viscosity of 0.73 dL/g) and 118.5 mL pure water were added together to a reactor equipped with a stirrer, and stirred till pullulan was completely dissolved. 120 g epoxide-activated wet gel (having a water content of 4.16) prepared in Reference Example 3 was added to the reactor. The inner temperature was adjusted to 30° C. with fully stirring. After stirring for 1 hr, 15.0 g of 45% aqueous NaOH solution was added and reacted for 18 hr. After the reaction, the reaction solution was filtered, and the residue was thoroughly washed with water, until the filtrate was neutral. After 30 minutes of suction-drying, 114.6 g pullulan-binding porous particles (having a water content of 4.10) were obtained.

11) Reference Example 11

60.0 g polymer dextran EH (manufactured by Meito Sangyo Co., Ltd., having a molecular weight equivalent to 200,000 and a limiting viscosity of 0.42 dL/g) and 142.9 mL pure water were added together to a reactor equipped with a stirrer, and stirred till polymer dextran EH was completely dissolved. 120 g epoxide-activated wet gel (having a water content of 3.75 and an epoxide group content of 297 µmol/g-dry) prepared as the same as Reference Example 1 was added to the reactor. The inner temperature was adjusted to 30° C. with fully stirring. After stirring for 1 hr, 16.5 g of 45% aqueous NaOH solution was added and reacted for 18 hr. After the reaction, the reaction solution was filtered, and the residue was thoroughly washed with water, until the filtrate was neutral. After 30 minutes of suction-drying, 116.7 g dextran binding porous particles were obtained.

12) Reference Example 12

42.4 g polymer dextran EH (manufactured by Meito Sangyo Co., Ltd., having a molecular weight equivalent to 200,000 and a limiting viscosity of 0.42 dL/g) and 142.9 mL pure water were added together to a reactor equipped with a stirrer, and stirred till polymer dextran EH was completely dissolved. 120 g epoxide-activated wet gel (having a water content of 3.75 and an epoxide group content of 297 µmol/g-dry) prepared as the same as Reference Example 1 was added to the reactor. The inner temperature was adjusted to 30° C. with fully stirring. After stirring for 1 hr, 16.5 g of 45% aqueous NaOH solution was added and reacted for 18 hr. After the reaction, the reaction solution was filtered, and the residue was thoroughly washed with water, until the filtrate was neutral. After 30 minutes of suction-drying, 117.8 g dextran binding porous particles were obtained.

(2) Sulfation of Reference Examples 4-12

1) Preparation Example 5

The air in a 500 ml separable flask equipped with a dropping funnel, a cooler condenser, a stirrer, and a thermometer was fully replaced with nitrogen, and 200 g dehydrated pyridine was added to the reactor, sealed with nitrogen, and then cooled to 5° C. Next, 5.99 g chlorosulfonic acid was added dropwise over 5 min through the dropping funnel, and the temperature in the reactor was raised to 65° C.±2° C. after stirring at 5° C.-10° C. for 1 hr. Afterwards, 30.5 g pullulan-binding porous particles (having a water content of 0.48%) prepared in Reference Example 4 and previously dried to a water content of 1% or less under reduced pressure of 13 Pa at 80° C. by using a vacuum drier was added to a reactor, and reacted for 4 hr. Then, the temperature in the reactor was cooled to 25° C., 40.9 g of 20% aqueous sodium hydroxide solution was added and stirred for 30 min, and then the reaction was stopped. After standing overnight, the reaction solution was filtered, and the residue was thoroughly washed with water, until the filtrate was neutral. After 15 minutes of suction-drying, 110.8 g chromatography medium (having a sulfur content in the dried gel of 2.4%) was obtained.

2) Preparation Example 6

The air in a 500 ml separable flask equipped with a dropping funnel, a cooler condenser, a stirrer, and a thermometer was fully replaced with nitrogen, and 201 g dehydrated pyridine was added to the reactor, sealed with nitrogen, and then cooled to 5° C. Next, 6.02 g chlorosulfonic acid was added dropwise over 5 min through the dropping funnel, and the temperature in the reactor was raised to 65° C.±2° C. after stirring at 5° C.-10° C. for 1 hr. Afterwards, 30.6 g pullulan-binding porous particles (having a water content of 0.45%) prepared in Reference Example 5 and previously dried to a water content of 1% or less under a reduced pressure of 13 Pa at 80° C. by using a vacuum drier was added to a reactor, and reacted for 4 hr. Then, the temperature in the reactor was cooled to 25° C., 41.1 g of 20% aqueous sodium hydroxide solution was added and stirred for 30 min, and then the reaction was stopped. After standing overnight, the reaction solution was filtered, and the residue was thoroughly washed with water, until the filtrate was neutral. After 15 minutes of suction-drying, 105.3 g chromatography medium (having a sulfur content in the dried gel of 1.1%) was obtained.

3) Preparation Example 7

The air in a 500 ml separable flask equipped with a dropping funnel, a cooler condenser, a stirrer, and a thermometer was fully replaced with nitrogen, and 206 g dehydrated pyridine was added to the reactor, sealed with nitrogen, and then cooled to 5° C. Next, 6.17 g chlorosulfonic acid was added dropwise over 5 min through the dropping funnel, and the temperature in the reactor was raised to 65° C.±2° C. after stirring at 5° C.-10° C. for 1 hr. Afterwards, 31.4 g pullulan-binding porous particles (having a water content of 0.70%) prepared in Reference Example 6 and previously dried to a water content of 1% or less under a reduced pressure of 13 Pa at 80° C. by using a vacuum drier was added to a reactor, and reacted for 4 hr. Then, the temperature in the reactor was cooled to 25° C., 42.1 g of 20% aqueous sodium hydroxide solution was added and stirred for 30 min, and then the reaction was stopped. After standing overnight, the reaction solution was filtered, and the residue was thoroughly washed with water, until the filtrate was neutral. After 15 minutes of suction-drying, 102.62 g chromatography medium (having a sulfur content in the dried gel of 0.8%) was obtained.

4) Preparation Example 8

The air in a 500 ml separable flask equipped with a dropping funnel, a cooler condenser, a stirrer, and a thermometer and stirred overnight was fully replaced with nitrogen, and 218 g dehydrated pyridine was added to the reactor, sealed with nitrogen, and then cooled to 5° C. Next, 6.54 g chlorosulfonic acid was added dropwise over 5 min through the dropping funnel, and the temperature in the reactor was raised to 65° C.±2° C. after stirring at 5° C.-10° C. for 1 hr. Afterwards, 33.4 g pullulan-binding porous particles (having a water content of 0.56%) prepared in Reference Example 7 and previously dried to a water content of 1% or less under a reduced pressure of 13 Pa at 80° C. by using a vacuum drier was added to a reactor, and reacted for 4 hr. Then, the temperature in the reactor was cooled to 25° C., 44.7 g of 20% aqueous sodium hydroxide solution was added and stirred for 30 min, and then the reaction was stopped. After standing overnight, the reaction solution was filtered, and the residue was thoroughly washed with water, until the filtrate was neutral. After 15 minutes of suction-drying, 135.1 g chromatography medium (having a sulfur content in the dried gel of 2.1%) was obtained.

5) Preparation Example 9

The air in a 500 ml separable flask equipped with a dropping funnel, a cooler condenser, a stirrer, and a thermometer was fully replaced with nitrogen, and 205 g dehydrated pyridine was added to the reactor, sealed with nitrogen, and then cooled to 5° C. Next, 6.14 g chlorosulfonic acid was added dropwise over 5 min through the dropping funnel, and the temperature in the reactor was raised to 65° C.±2° C. after stirring at 5° C.-10° C. for 1 hr. Afterwards, 31.2 g pullulan binding porous particles (having a water content of 0.56%) prepared in Reference Example 8 and previously dried to a water content of 1% or less under a reduced pressure of 13 Pa at 80° C. by using a vacuum drier was added to a reactor, and reacted for 4 hr. Then, the temperature in the reactor was cooled to 25° C., 41.9 g of 20% aqueous sodium hydroxide solution was added and stirred for 30 min, and then the reaction was stopped. After standing overnight, the reaction solution was filtered, and the residue was thoroughly washed with water, until the filtrate was neutral. After 15 minutes of suction-drying, 132.9 g chromatography medium (having a sulfur content in the dried gel of 2.1%) was obtained.

6) Preparation Example 10

The air in a 500 ml separable flask equipped with a dropping funnel, a cooler condenser, a stirrer, and a thermometer was fully replaced with nitrogen, and 213 g dehydrated pyridine was added to the reactor, sealed with nitrogen, and then cooled to 5° C. Next, 6.39 g chlorosulfonic acid was added dropwise over 5 min through the dropping funnel, and the temperature in the reactor was raised to 65° C.±2° C. after stirring at 5° C.-10° C. for 1 hr. Afterwards, 32.5 g pullulan-binding porous particles (having a water content of 0.48%) prepared in Reference Example 9 and previously dried to a water content of 1% or less under reduced pressure of 13 Pa at 80° C. by using a vacuum drier was added to a reactor, and reacted for 4 hr. Then, the temperature in the reactor was cooled to 25° C., 43.6 g of 20% aqueous sodium hydroxide solution was added and stirred for 30 min, and then the reaction was stopped. After standing overnight, the reaction solution was filtered, and the residue was thoroughly washed with water, until the filtrate was neutral. After 15 minutes of suction-drying, 127.4 g chromatography medium (having a sulfur content in the dried gel of 1.4%) was obtained.

7) Preparation Example 11

The air in a 500 ml separable flask equipped with a dropping funnel, a cooler condenser, a stirrer, and a thermometer was fully replaced with nitrogen, and 172 g dehydrated pyridine was added to the reactor, sealed with nitrogen, and then cooled to 5° C. Next, 5.17 g chlorosulfonic acid was added dropwise over 5 min through the dropping funnel, and the temperature in the reactor was raised to 65° C.±2° C. after stirring at 5° C.-10° C. for 1 hr. Afterwards, 26.3 g pullulan-binding porous particles (having a water content of 0.40%) prepared in Reference Example 10 and previously dried to a water content of 1% or less under a reduced pressure of 13 Pa at 80° C. by using a vacuum drier was added to a reactor, and reacted for 4 hr. Then, the temperature in the reactor was cooled to 25° C., 35.3 g of 20% aqueous sodium hydroxide solution was added and stirred for 30 min, and then the reaction was stopped. After standing overnight, the reaction solution was filtered, and the residue was thoroughly washed with water, until the filtrate was neutral. After 15 minutes of suction-drying, 98.8 g chromatography medium (having a sulfur content in the dried gel of 1.0%) was obtained.

8) Preparation Example 12

The air in a 500 ml separable flask equipped with a dropping funnel, a cooler condenser, a stirrer, and a thermometer was fully replaced with nitrogen, and 183 g dehydrated pyridine was added to the reactor, sealed with nitrogen, and then cooled to 5° C. Next, 5.48 g chlorosulfonic acid was added dropwise over 5 min through the dropping funnel, and the temperature in the reactor was raised to 65° C.±2° C. after stirring at 5° C.-10° C. for 1 hr. Afterwards, 27.87 g dextran-binding porous particles (having a water content of 0.63%) prepared in Reference Example 11 and previously dried to a water content of 1% or less under a reduced pressure of 13 Pa at 80° C. by using a vacuum drier was added to a reactor, and reacted for 4 hr. Then, the temperature in the reactor was cooled to 25° C., 37.4 g of 20% aqueous sodium hydroxide solution was added and stirred for 30 min, and then the reaction was stopped. After standing overnight, the reaction solution was filtered, and the residue was thoroughly washed with water until the filtrate was neutral. After 15 minutes of suction-drying, 99.8 g chromatography medium (having a sulfur content in the dried gel of 0.9%) was obtained.

9) Preparation Example 13

The air in a 500 ml separable flask equipped with a dropping funnel, a cooler condenser, a stirrer, and a thermometer and stirred overnight was fully replaced with nitrogen, and 180 g dehydrated pyridine was added to the reactor, sealed with nitrogen, and then cooled to 5° C. Next, 5.39 g chlorosulfonic acid was added dropwise over 5 min through the dropping funnel, and the temperature in the reactor was raised to 65° C.±2° C. after stirring at 5° C.-10° C. for 1 hr. Afterwards, 27.40 g dextran-binding porous particles (having a water content of 0.52%) prepared in Reference Example 12 and previously dried to a water content of 1% or less under a reduced pressure of 13 Pa at 80° C. by using a vacuum drier was added to a reactor, and reacted for 4 hr. Then, the temperature in the reactor was cooled to 25° C., 36.8 g of 20% aqueous sodium hydroxide solution was added and stirred for 30 min, and then the reaction was stopped. After standing overnight, the reaction solution was filtered, and the residue was thoroughly washed with water, until the filtrate was neutral. After 15 minutes of suction-drying, 102.6 g chromatography medium (having a sulfur content in the dried gel of 1.6%) was obtained.

7. Virus Adsorption Test 2

(1) Virus Adsorption Test Using Chromatography medium of Preparation Example 9

The chromatography medium of Preparation Example 9 was used as medium.

The chromatography medium of Preparation Example 9 was dispersed in water, and degassed with stirring under vacuum. Then, a column of Φ3×50 mm was packed with the chromatography medium, and mounted on a Biologic LP System (manufactured by Bio-Rad Co., Ltd.). Next, 0.01 M phosphate buffer (pH 7.4) of 10 times of the column volume or above was flowed through the column to make the column to be equilibrated. Afterwards, 10 mL test virus solution of H7N7 strain (having a total HA titer in use of 51200) filtered by a membrane filter (product name: DISMIC-25cs, manufactured by Advantec Co., Ltd.) made of cellulose acetate was flowed through the column, and at the same time, the effluent from the column was recovered in a unit of 1 mL.

After the flowing of the test virus solution, 0.01 M phosphate buffer −0.19M NaCl (pH 7.2) was flowed to wash off the non-adsorbed portion. Then, 0.01 M phosphate buffer −3M NaCl (pH 7.0) was flowed until the virus adsorbed on the column was completely eluted. Afterwards, the HA titer of the recovered effluent was measured, to calculate the 10% DBC. The result shows that the 10% DBC is 38608 HA/mL-gel.

(2) Virus Adsorption Test Using the chromatography medium of Preparation Examples 5-8 and 10-12

This test was performed following the virus adsorption test described above, except that the chromatography medium of Preparation Examples 5-12 were used as the medium instead of the chromatography medium of Preparation Example 9. The result shows that the 10% DBC is 41514 HA/mL-gel when chromatography medium of Preparation Examples 5, 6, 7, 11 and 12 are used, and is 55352 HA/mL-gel when the chromatography medium of Preparation Examples 8 and 10 are used.

(3) Competitive Experiment 1 (Commercially Available Cellufine Sulfate)

This test was performed following the virus adsorption test described above, except that the chromatography medium of Preparation Examples 9 was replaced by the commercially available Cellufine Sulfate (control medium, manufactured by Chisso Corp., having a sulfur content in the dry gel of 0.09%). The result shows that the 10% DBC is 27676 HA/mL-gel when the commercially available Cellufine Sulfate is used as chromatography medium.

As shown in Table 2, all the chromatography medium of Preparation Examples 5-12 in the present invention adsorb influenza virus with high efficiency and exhibit a value of 1.4-2 times with respect to the virus adsorption ratio expressed as 10% DBC HA titer/ml, compared with the commercially available Cellufine Sulfate.

8. Evaluation of Nucleic Acid Adsorption Accompanying Virus Purification

The amount of nucleic acid in this embodiment was determined by using Quant-iT PicoGreen dsDNA Reagent and Kits commercially available from Invitrogen Corp.

Nucleic Acid Adsorption Experiment

The chromatography medium of Preparation Example 13 was used as medium.

The trial-produced medium was dispersed in water, and degassed with stirring under vacuum. Then, a column of Φ8×20 mm was packed with the chromatography medium, and mounted on a Biologic LP System (manufactured by Bio-Rad Co., Ltd.). Next, 0.01 M phosphate buffer (having a pH value of 7.4) of 10 times of the column volume or above was flowed through the column to make the column to be equilibrated. Afterwards, 8 mL test virus solution of H7N7 strain (having a total HA titer in use of 92160 and a total amount of nuclei acid of 11210 ng) filtered by a membrane filter (product name: DISMIC-25cs, manufactured by Advantec Co., Ltd.) made of cellulose acetate was flowed through the column, and at the same time, the effluent from the column was recovered in a unit of 1 mL. After the flowing of the test virus solution, 35 ml of 0.01 M phosphate buffer-0.19M NaCl (pH 7.2) was flowed to wash off the non-adsorbed portion. Then, 25 ml of 0.01 M phosphate buffer solution-3M NaCl (pH 7.0) was flowed to elute out the virus. Afterwards, the amount of nucleic acid in the effluent recovered was quantified. The result shows that the total amount of nucleic acid in the portion eluted is 935 ng, and the total HA titer is 77440.

(2) Competitive Experiment 2 (Commercially Available Cellufine Sulfate)

This experiment was performed following the nucleic acid adsorption experiment described above, except that the chromatography medium of Preparation Examples 9 was replaced by the commercially available Cellufine Sulfate (manufactured by Chisso Corp., having a sulfur content of 0.09%). The result shows that the total amount of nucleic acid in the portion eluted from the commercially available Cellufine Sulfate is 1474 ng, and the total HA titer is 80080.

Based on this result, compared to the commercially available Cellufine Sulfate used as control, the chromatography medium can reduce the nucleic acid adsorption by about 63%, while exhibiting a substantially equal virus adsorption capability.

TABLE 2

| Preparation Example | Reference Example as Raw Material | Species of Polysaccharide Used | Sulfur Content (%) | 10% DBC HA Titter/ ml-gel | Ratio to Control |
| --- | --- | --- | --- | --- | --- |
| Preparation Example 5 | Reference Example 4 | pullulan | 2.4 | 41514 | 150 |
| Preparation Example 6 | Reference Example 5 | pullulan | 1.1 | 41514 | 150 |
| Preparation Example 7 | Reference Example 6 | pullulan | 0.8 | 41514 | 150 |
| Preparation Example 8 | Reference Example 7 | pullulan | 2.1 | 55352 | 200 |
| Preparation Example 9 | Reference Example 8 | pullulan | 2.1 | 38608 | 140 |
| Preparation Example 10 | Reference Example 9 | pullulan | 1.4 | 55352 | 200 |
| Preparation Example 11 | Reference Example 10 | pullulan | 1.0 | 41514 | 150 |
| Preparation Example 12 | Reference Example 11 | dextran | 0.9 | 41514 | 150 |
| Competitive Packing material | Commercially Cellufine Sulfate | No | 0.09 | 27676 | 100 |

It will be apparent to those skilled in the art that various modifications and variations can be made to the structure of the present invention without departing from the scope or spirit of the invention. In view of the foregoing, it is intended that the present invention cover modifications and variations of this invention provided they fall within the scope of the following claims and their equivalents.

What is claimed is:

1. A chromatography medium, formed by binding a sulfated polysaccharide to porous particles having an exclusion limit molecular weight of 6000 Da or less when pure water is used as mobile phase and standard polyethylene glycol is used, wherein the chromatography medium is of General Formula (1) below:

$$X\text{—}O\text{—}CH_2\text{—}C(OH)H\text{—}CH_2\text{—}NH\text{—}CH_2\text{—}Z \quad (1)$$

wherein in Formula (1), X is the porous particle have an average particle size in the range of 30-200 μm, bonded to X is an oxygen originating from hydroxyl of the porous particle, Z is the sulfated polysaccharide, and C bonded to Z is a carbon originating from the reductive end of the sulfated polysaccharide, wherein sulfated polysaccharide is a ligand, and a limiting viscosity of the sulfated polysaccharide is in the range of 0.40-0.90 dL/g.

2. The chromatography medium according to claim 1, wherein the porous particles are cellulose particles.

3. The chromatography medium according to claim 1, wherein the sulfated polysaccharide is one or more selected from cellulose sulfate, dextran sulfate, and pullulan sulfate.

4. The chromatography medium according to claim 1, wherein a content of sulfur is in a range of 0.2-6 wt %.

5. The chromatography medium according to claim 3, wherein the sulfated polysaccharide is cellulose sulfate and the cellulose sulfate has a sulfur content of 15 wt % or more, and a viscosity of an aqueous solution of 1 wt % at 20° C. in the range of 15-300 mPa/sec.

* * * * *